United States Patent
Osmulski et al.

(10) Patent No.: US 10,167,259 B2
(45) Date of Patent: Jan. 1, 2019

(54) ALLOSTERIC INHIBITORS OF PROTEASOME AND METHODS OF USE THEREOF

(71) Applicant: THE BOARD OF REGENTS OF THE UNIVERSITY OF TEXAS SYSTEM, Austin, TX (US)

(72) Inventors: Pawel A. Osmulski, San Antonio, TX (US); Maria E. Gaczynska, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/896,984

(22) PCT Filed: Jun. 13, 2014

(86) PCT No.: PCT/US2014/042383
§ 371 (c)(1),
(2) Date: Dec. 9, 2015

(87) PCT Pub. No.: WO2014/201405
PCT Pub. Date: Dec. 18, 2014

(65) Prior Publication Data
US 2016/0152567 A1      Jun. 2, 2016

Related U.S. Application Data

(60) Provisional application No. 61/835,221, filed on Jun. 14, 2013.

(51) Int. Cl.
| | |
|---|---|
| C07D 211/60 | (2006.01) |
| A61K 45/06 | (2006.01) |
| A61K 31/69 | (2006.01) |
| C07D 401/12 | (2006.01) |
| C07D 413/12 | (2006.01) |
| C07D 498/08 | (2006.01) |

(52) U.S. Cl.
CPC ............ *C07D 211/60* (2013.01); *A61K 31/69* (2013.01); *A61K 45/06* (2013.01); *C07D 401/12* (2013.01); *C07D 413/12* (2013.01); *C07D 498/08* (2013.01)

(58) Field of Classification Search
CPC .................................................... C07D 211/60
See application file for complete search history.

(56) References Cited

U.S. PATENT DOCUMENTS

| | | | |
|---|---|---|---|
| 5,620,971 A | 4/1997 | Armistead et al. | |
| 6,187,784 B1 * | 2/2001 | Steiner ................. | A61K 8/4913 514/248 |
| 6,335,348 B1 | 1/2002 | Ross et al. | |
| 6,376,517 B1 | 4/2002 | Ross et al. | |
| 7,056,935 B2 | 6/2006 | Steiner et al. | |
| 7,265,150 B1 | 9/2007 | Ross et al. | |

FOREIGN PATENT DOCUMENTS

| | | | |
|---|---|---|---|
| WO | WO 99/62881 | * | 12/1999 |
| WO | WO 2002/096420 | | 12/2002 |
| WO | WO 2012/075048 | | 6/2012 |
| WO | WO 2013/091900 | | 6/2013 |

OTHER PUBLICATIONS

Jankowska, et al., "Potential allosteric modulators of the proteasome activity," *Biopolymers*, 93:481-495, 2010.
Lander, et al., "Complete subunit architecture of the proteasome regulatory particle," *Nature*, 482:186-191, 2009.
Liang, et al., "Refined structure of the FKBP12-rapamycin-FRB ternary complex at 2.2 A resolution," *Acta Crystallographica Section D: Biological Crystallography*, 55(Pt. 4):736-44, 1999.
Ma and Blenis, "Molecular mechanisms of mTOR-mediated translational control," *Nature Reviews in Molecular and Cell Biology*, 10:307-318, 2009.
Osmulski and Gaczynska, "Rapamycin allosterically inhibits the proteasome," *Molecular Pharmacology*, 84:104-113, 2013.
Osmulski, et al., "A tetrahedral transition state at the active sites of the 20S proteasome is coupled to opening of the alpha-ring channel," *Structure*, 17(18):1137-47, 2009.
PCT International Search Report and Written Opinion issued in International Application No. PCT/US2014/042383, dated Sep. 30, 2014.
Extended European Search Report issued in European Patent Application No. 14811064.6, dated Jan. 2, 2017.
Gopalakrishnan et al., "Evaluation of synthetic FK506 analogues as ligands for the FK506-binding proteins 51 and 52," *Journal of Medicinal Chemistry*, 55(9):4114-4122, 2012.
Hamilton et al., "Immunophilins: beyond immunosuppression," *Journal of Medicinal Chemistry*, 41(26):5119-5143, 1998.
Hamilton et al., "Synthesis of N-glyoxyl prolyl and pipecolyl amides and thioesters and evaluation of their in vitro and in vivo nerve regenerative effects," *Journal of Medicinal Chemistry*, 45(16):3549-3557, 2002.
Holt et al., "Design, synthesis, and kinetic evaluation of high-affinity FKBP ligands and the x-ray crystal structures of their complexes with FKBP12," *Journal of the American Chemical Society*, 115(22):9925-9938, 1993.
Leach et al., "Fragment screening: an introduction," *Molecular Biosystems*, 2(9):429-446, 2006.

* cited by examiner

*Primary Examiner* — Yong S. Chong
(74) *Attorney, Agent, or Firm* — Parker Highlander PLLC

(57) ABSTRACT

The present invention relates generally to novel allosteric regulators of proteasome activity, methods for preparation and use, and pharmaceutical compositions thereof. Specifically piperidine-2-carboxylic acid derivatives containing 1-oxo-aroyl group and a lipophilic ester side chain are disclosed as allosteric inhibitors of proteasome 2S activity, and as therapeutic agents for the treatment of proteasome-associated disorders in a subject.

16 Claims, 7 Drawing Sheets

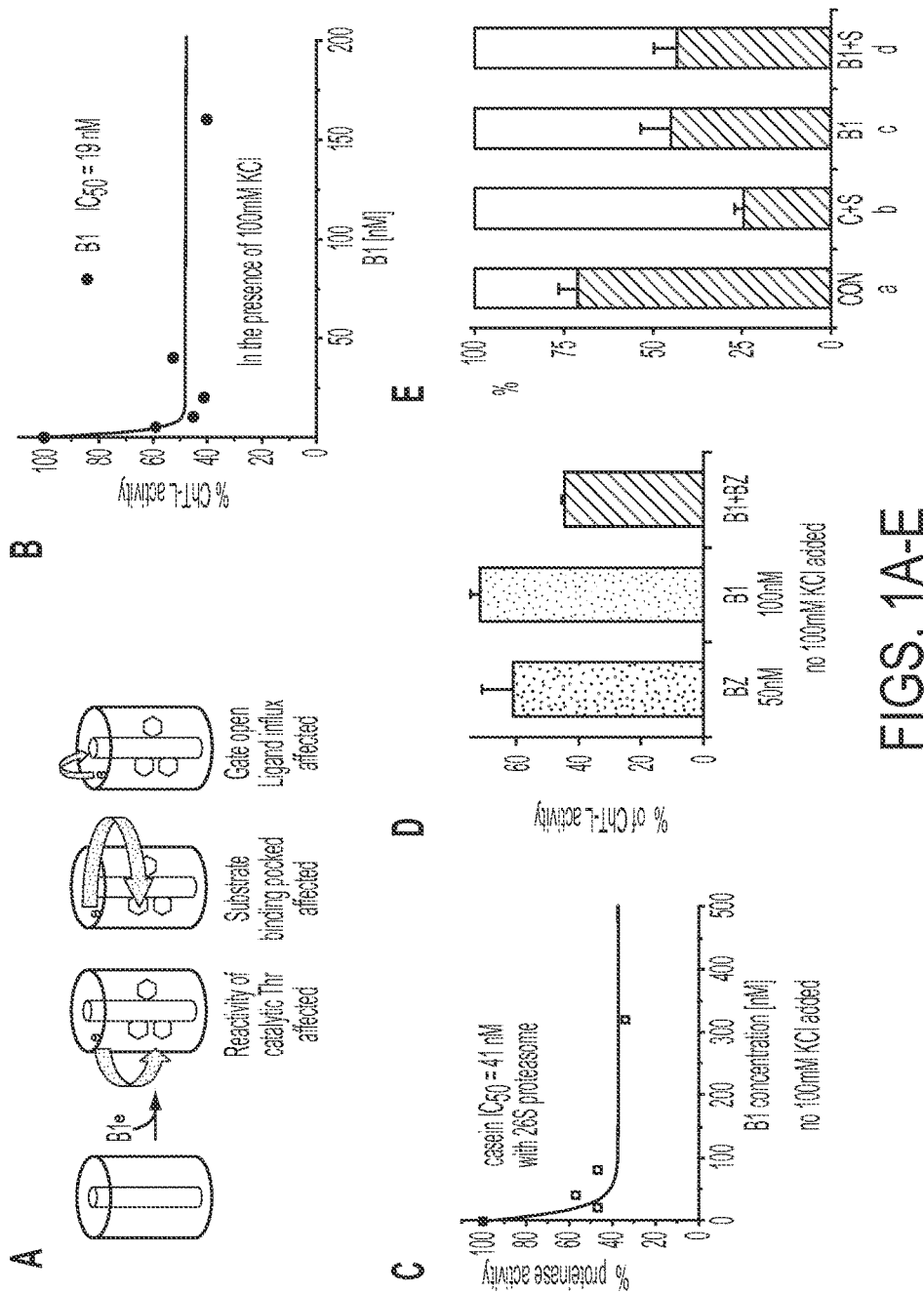
FIGS. 1A-E

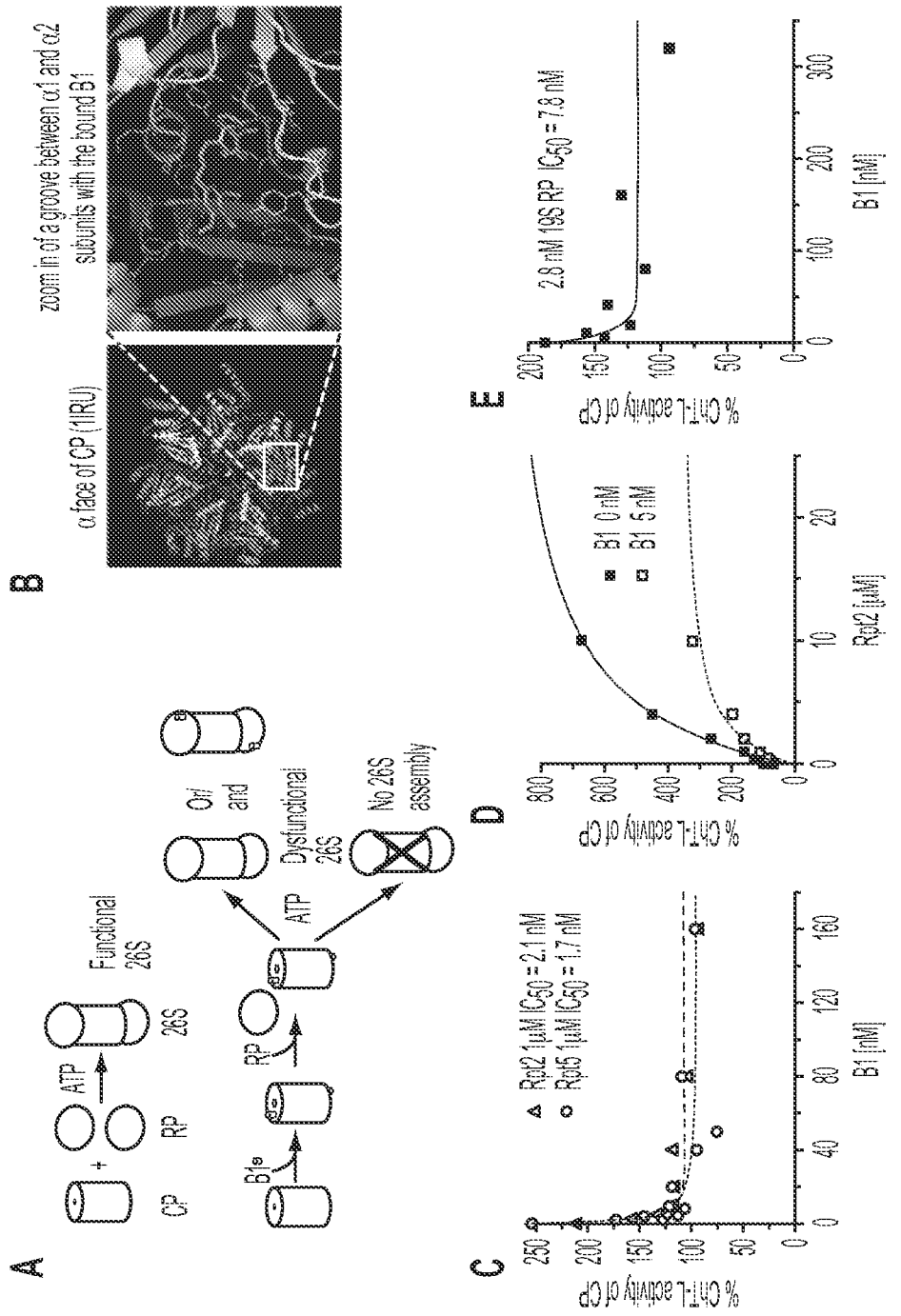
FIGS. 2A-E

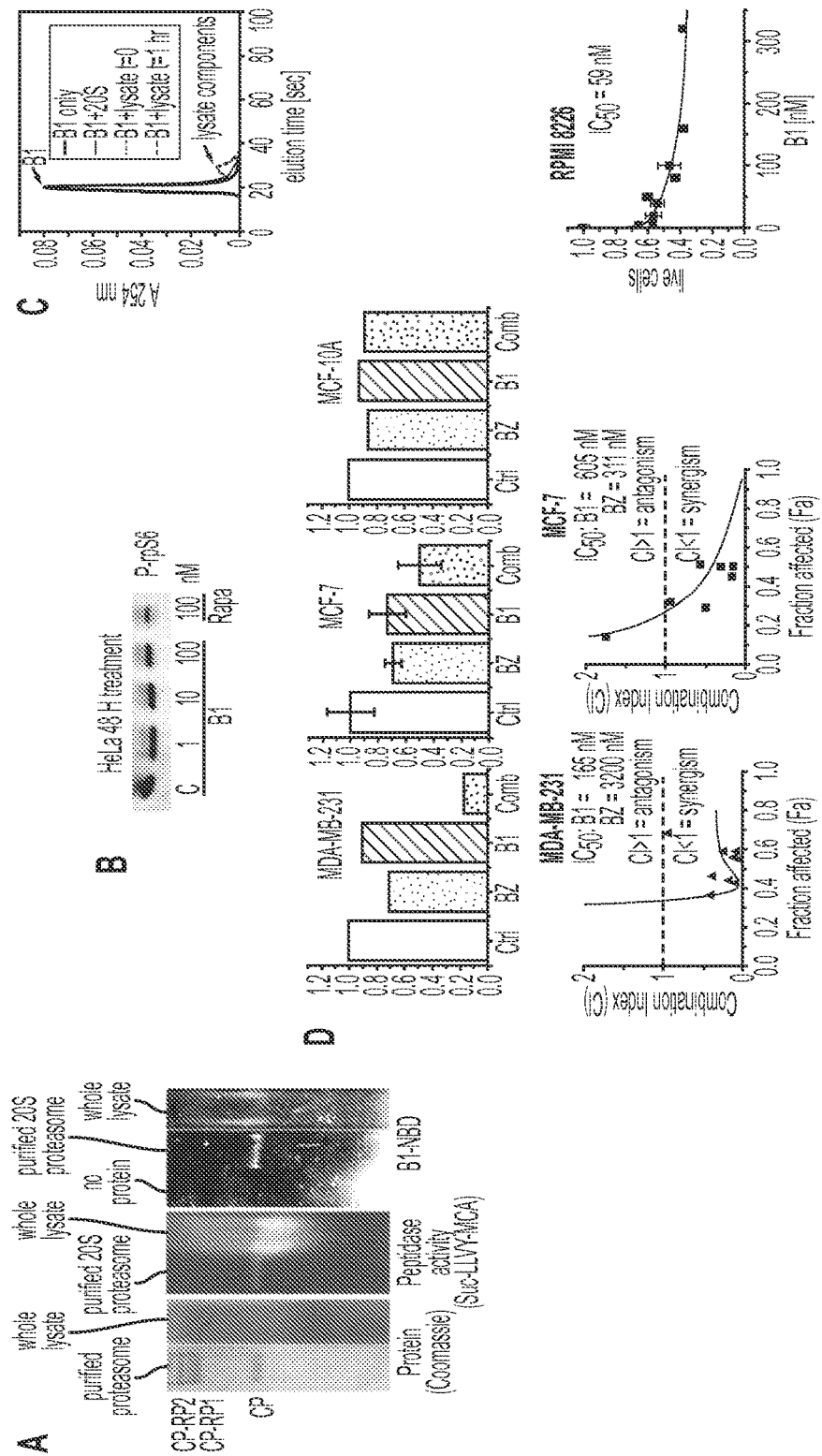
FIGS. 3A-D

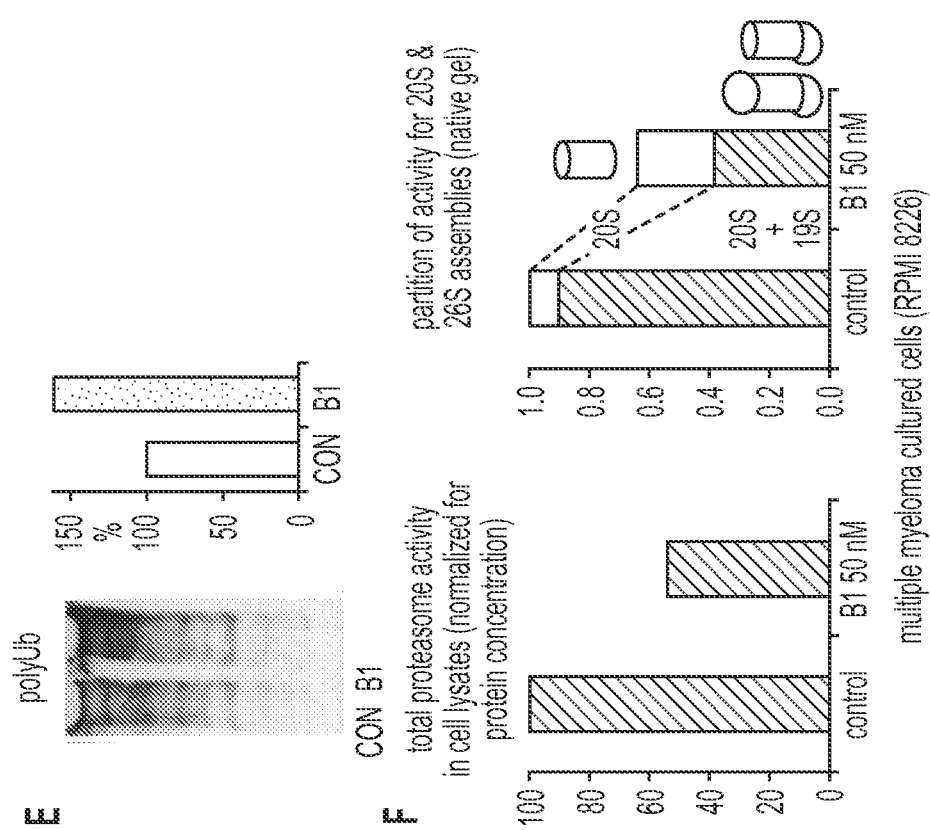
FIGS. 3E-F

ALLOSTERIC INHIBITORS OF PROTEASOME AND METHODS OF USE THEREOF

This application is a national phase application under 35 U.S.C. § 371 of International Application No. PCT/US2014/042383, filed Jun. 13, 2014, which claims priority to U.S. Provisional Application Ser. No. 61/835,221 filed Jun. 14, 2013. The entire contents of the above-referenced disclosures are specifically incorporated herein by reference.

BACKGROUND OF THE INVENTION

I. Field of the Invention

The present invention relates generally to novel proteasome allosteric inhibitors, their use in pharmaceutical compositions, and methods of using the compounds for treating diseases, thereof.

II. Description of Related Art

The enzyme, proteasome, is an essential protease of the ubiquitin-proteasome pathway (UPP) degrading the bulk of intracellular proteins, including vital regulatory factors and damaged polypeptides (Jankowska, et al., 2013). Because of its multifaceted physiological role, which includes regulation of apoptosis, inhibition of proteasome became an attractive intervention to stop cancer (Crawford, et al., 2011). Two FDA-approved proteasome-targeting drugs, bortezomib/Velcade and PR-171/Kyprolis, and several others in clinical trials, compete with proteasome's physiological substrates by blocking its active centers. The inhibition induces apoptosis, as the inactive enzyme fails to degrade IκB and activate NFκB, stabilizes pro-apoptotic proteins, and leaves the cell overloaded with non-degraded polypeptides (Crawford, et al., 2011). These proteasome inhibitors are effective in treatment of blood cancers characterized by high levels of both NFκB and proteasomes (Crawford, et al., 2011; Busse, et al., 2008; Kraus, et al., 2007). Similar up-regulation has been found in subsets of breast cancers (Yamaguchi, et al., 2009; Chen and Madura, 2005), however, there is no evidence of advantage of bortezomib treatment in these or other breast cancer subtypes (Yang, et al., 2006; Engel, et al., 2007). The discovery of the new mechanism of proteasome inhibition introduces a unique opportunity to broaden the list of cancers strongly responding to anti-proteasome therapy.

The proteasome is a complex and diverse enzymatic factory often compared to a molecular organelle (Groll, et al., 2005). All proteasome assemblies contain a tube-shaped 20S (700 kDa) catalytic core (CP) constructed from four hetero heptameric rings. The external α rings form the α face that binds protein complexes regulating the catalysis. The center of the α ring is occupied by an allosterically regulated gate, which provides the passage to the central channel leading to the catalytic chamber built with β-rings (Groll, et al., 2005; Osmulski, et al., 2009). In the Eukaryota there are three pairs of active centers of the N-terminal Thr type that cleave peptide bonds on the carboxyl site of hydrophobic (chymotrypsin-like: ChT-L), basic (trypsin-like: T-L), and acidic (PGPH) amino acids. All clinically relevant proteasome inhibitors target primarily the "workhorse" chymotrypsin-like activity. The 26S assembly, built from CP and at least one 19S regulatory particle (FIG. 1), is the most physiologically significant proteasome since it is the only enzymes in the cell capable of processing protein substrates tagged for degradation by polyubiquitin (Groll, et al., 2005; Madura, 2009). De novo formation of multisubunit RP is a multistep process assisted by several chaperones (Madura, 2009). However, the assembled RP may undergo multiple cycles of association dissociation with CP (Babbitt, et al., 2005). Stability of 26S complex, important for its performance, is regulated by ATP (Liu, et al., 2006), bortezomib (stabilization (Klejinen, et al., 2007)), and by allosteric ligands (Gaczynska, et al., 2003). Other modules binding to the α face include 11S and PA200 activators and PI31 "proteasome inhibitor." The modules utilize grooves between α subunits for binding to CP, and all except 11S anchor via HbYX (hydrophobic-Tyr-any amino acid) C-terminal motifs (Jankowska, et al., 2013; Smith, 2007). However, new and improved molecules for modulating proteasome function are needed.

SUMMARY OF THE INVENTION

In some aspects of the present invention, there is provided a compound of the formula:

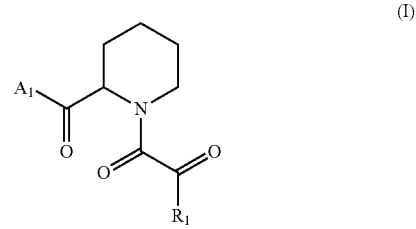

wherein: $A_1$ is hydroxy, amino, or

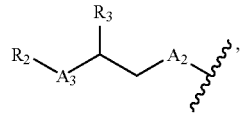

wherein: $A_2$ is —O— or —$NR_6$— wherein $R_6$ is hydrogen, alkyl$_{(C \le 6)}$ or substituted alkyl$_{(C \le 6)}$; $A_3$ is alkanediyl$_{(C \le 6)}$, alkenediyl$_{(C \le 6)}$, or a substituted version of either of these groups; $R_2$ is

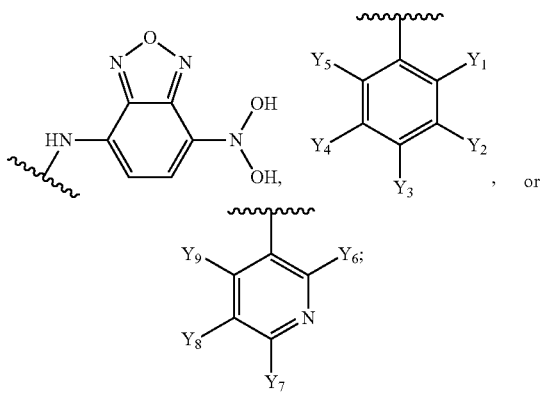

wherein: $Y_1$, $Y_2$, $Y_3$, $Y_4$, $Y_5$, $Y_6$, $Y_7$, $Y_8$, and $Y_9$ are each independently hydrogen, hydroxy, phosphate, halo, alkyl$_{(C \le 12)}$, alkoxy$_{(C \le 12)}$, acyloxy$_{(C \le 12)}$, heteroaryl$_{(C \le 12)}$, acyl$_{(C \le 12)}$, alkylamino$_{(C \le 12)}$, dialkylamino$_{(C \le 12)}$, or a substituted version of any of these groups; $R_3$ is hydrogen, alkyl$_{(C \le 8)}$, or a substituted alkyl$_{(C \le 8)}$; and $R_1$ is

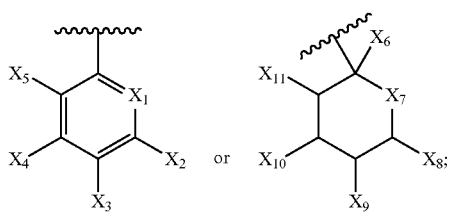

wherein: $X_1$ is O, N, or $CR_4$; $X_2$, $X_3$, $X_4$, $X_5$, and $R_4$ are each independently hydrogen, hydroxy, phosphate, halo, alkyl$_{(C\leq12)}$, alkoxy$_{(C\leq12)}$, acyloxy$_{(C\leq12)}$, heteroaryl$_{(C\leq12)}$, acyl$_{(C\leq12)}$, alkylamino$_{(C\leq12)}$, dialkylamino$_{(C\leq12)}$, or a substituted version of any of these groups; $X_6$ is hydrogen or hydroxy; $X_7$ is O, NH, or $C(R_5)_2$; $X_8$, $X_9$, $X_{10}$, $X_{11}$, and $R_5$ are each independently hydrogen, hydroxy, phosphate, halo, alkyl$_{(C\leq12)}$, alkoxy$_{(C\leq12)}$, acyloxy$_{(C\leq12)}$, heteroaryl$_{(C\leq12)}$, acyl$_{(C\leq12)}$, alkylamino$_{(C\leq12)}$, dialkylamino$_{(C\leq12)}$, or a substituted version of any of these groups; or a pharmaceutically acceptable salt thereof. In some embodiments, the compound is further defined as:

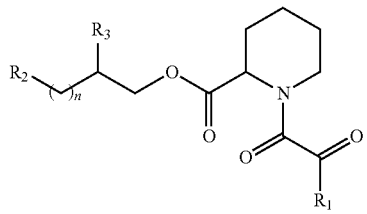

(II)

wherein: n is 1-4; $R_1$ is as defined earlier; $R_2$ is

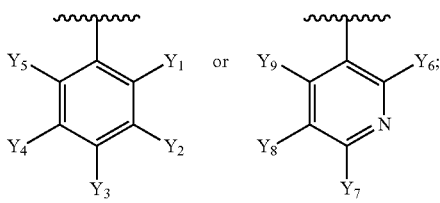

wherein: $Y_1$, $Y_2$, $Y_3$, $Y_4$, $Y_5$, $Y_6$, $Y_7$, $Y_8$, and $Y_9$ are each independently hydrogen, hydroxy, phosphate, halo, alkyl$_{(C\leq12)}$, alkoxy$_{(C\leq12)}$, acyloxy$_{(C\leq12)}$, heteroaryl$_{(C\leq12)}$, acyl$_{(C\leq12)}$, alkylamino$_{(C\leq12)}$, dialkylamino$_{(C\leq12)}$, or a substituted version of any of these groups; $R_3$ is hydrogen, alkyl$_{(C\leq8)}$, or a substituted alkyl$_{(C\leq8)}$; or a pharmaceutically acceptable salt, thereof. In some embodiments, n is 1. In other embodiments, n is 2. In other embodiments, n is 3. In other embodiments, n is 4. In some embodiments, $R_1$ is

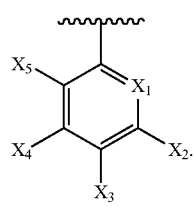

In some embodiments, $X_1$ is $CR_4$. In some embodiments, $R_4$ is hydrogen. In some embodiments, $X_2$, $X_3$, and $X_4$ are hydrogen. In other embodiments, $X_2$, $X_3$, and $X_4$ are alkoxy$_{(C\leq12)}$. In some embodiments, $X_2$, $X_3$, and $X_4$ are methoxy. In some embodiments, $X_5$ is hydrogen. In other embodiments, $R_1$ is

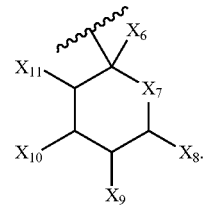

In some embodiments, $X_6$ is hydrogen. In other embodiments, $X_6$ is hydroxy. In some embodiments, $X_7$ is $C(R_5)_2$. In some embodiments, $R_5$ is hydrogen. In some embodiments, $X_8$, $X_9$, and $X_{10}$ are hydrogen. In some embodiments, $X_{11}$ is hydrogen. In some embodiments, $R_2$ is

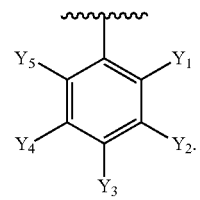

In some embodiments, $Y_1$ is hydrogen. In some embodiments, $Y_2$, $Y_3$, and $Y_4$ are hydrogen. In other embodiments, $Y_2$ is alkoxy$_{(C\leq12)}$. In other embodiments, $Y_3$ is alkoxy$_{(C\leq12)}$. In other embodiments, $Y_4$ is alkoxy$_{(C\leq12)}$. In still other embodiments, $Y_2$, $Y_3$, and $Y_4$ are alkoxy$_{(C\leq12)}$. In other embodiment, $Y_2$, $Y_3$, and $Y_4$ are methoxy. In other embodiments, $Y_3$ is methoxy. In some embodiments, $Y_5$ is hydrogen. In other embodiments, $Y_5$ is alkoxy$_{(C\leq12)}$. In other embodiments, $Y_5$ is methoxy. In other embodiments, $Y_2$ and $Y_5$ are alkoxy$_{(C\leq12)}$. In other embodiments, $Y_2$ and $Y_5$ are methoxy. In other embodiments, $R_2$ is

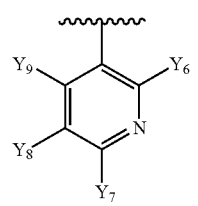

In some embodiments, $Y_6$ is hydrogen. In some embodiments, $Y_7$ and $Y_8$ are hydrogen. In other embodiments, $Y_7$ is alkoxy$_{(C\leq12)}$. In other embodiments, $Y_8$ is alkoxy$_{(C\leq12)}$. In other embodiments, $Y_7$ and $Y_8$ are alkoxy$_{(C\leq12)}$. In other embodiments, $Y_7$ and $Y_8$ are methoxy. In some embodiments, $Y_9$ is hydrogen. In some embodiments, $R_3$ is hydrogen. In other embodiments, $R_3$ is alkyl$_{(C\leq8)}$. In other embodiments, $R_3$ is methyl.

In some embodiments, the compounds are further defined as:
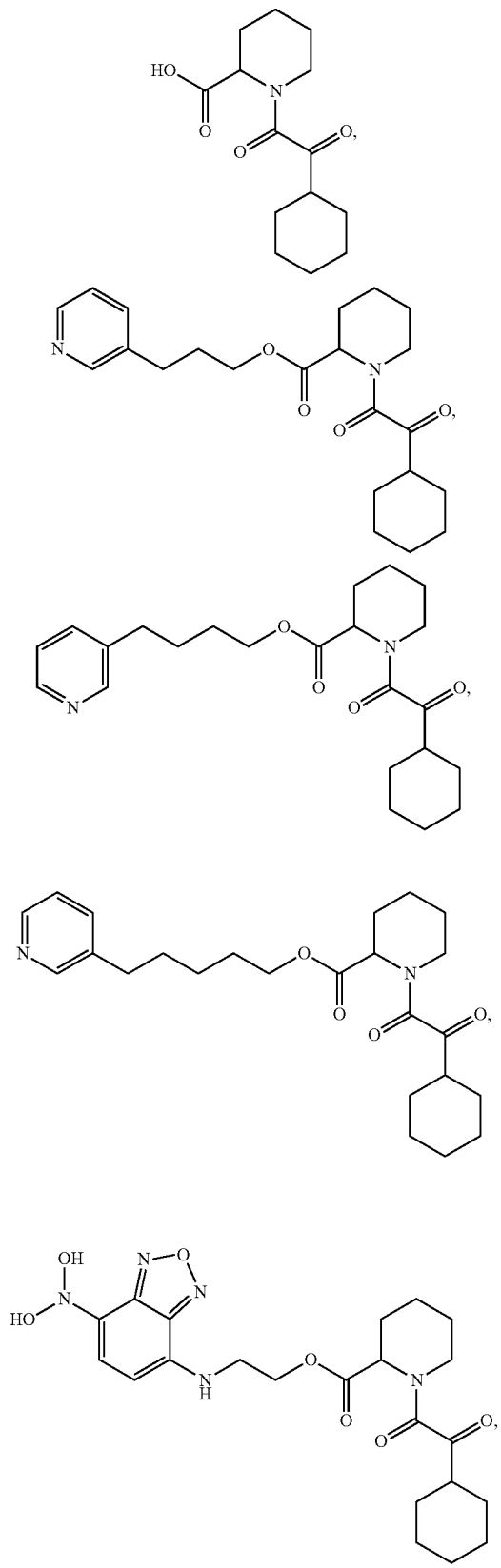
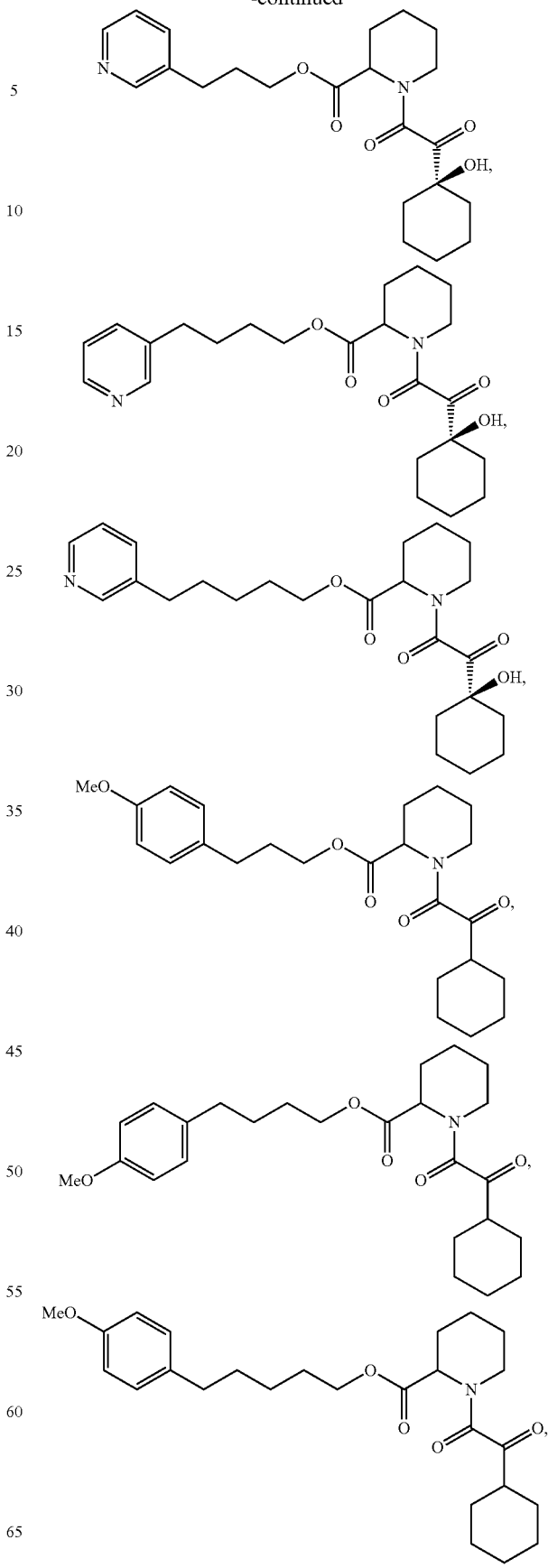

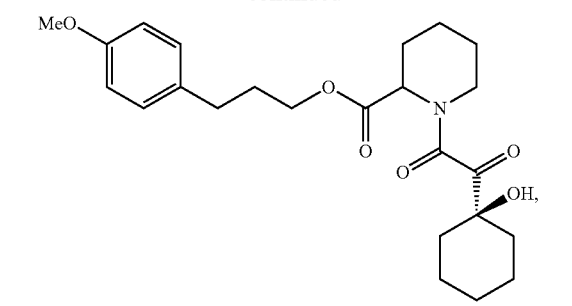
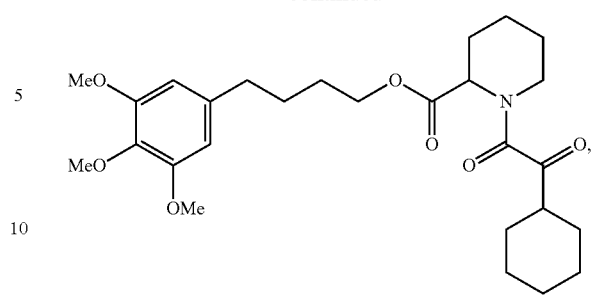
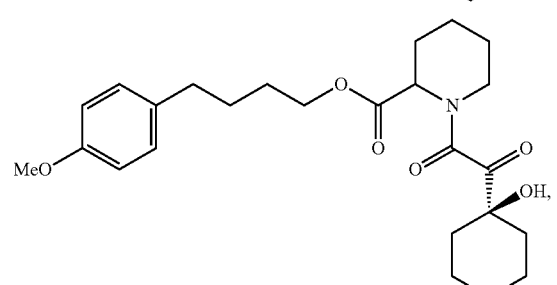
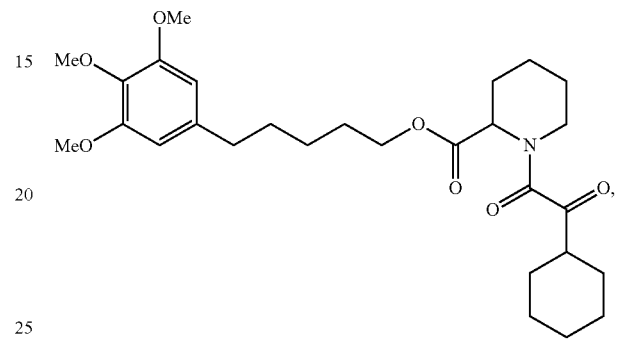
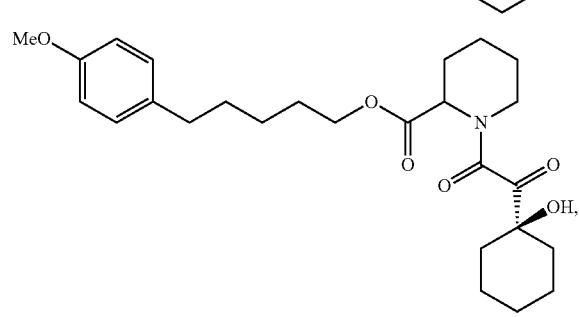
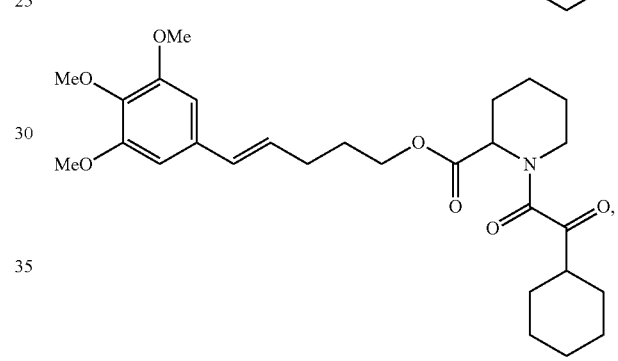
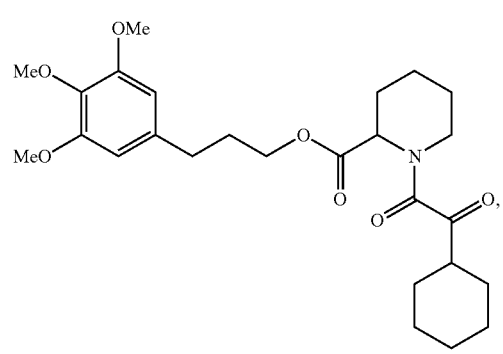
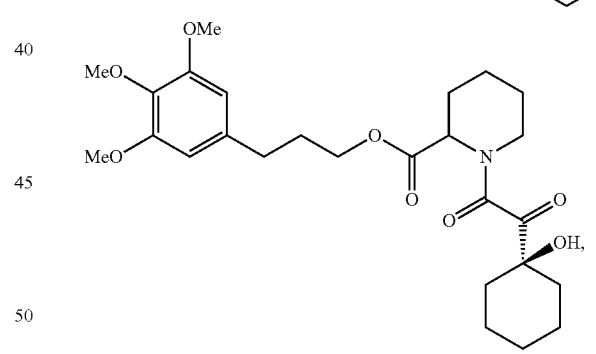
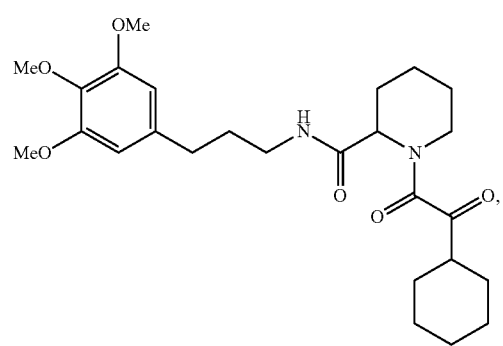
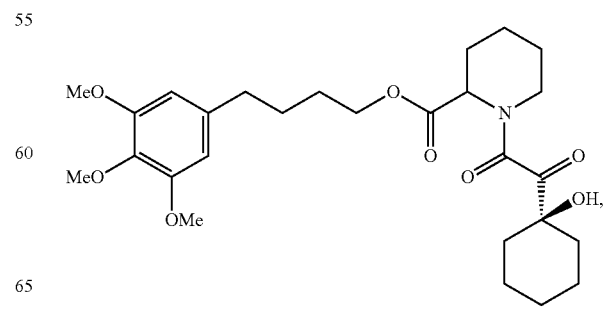

-continued
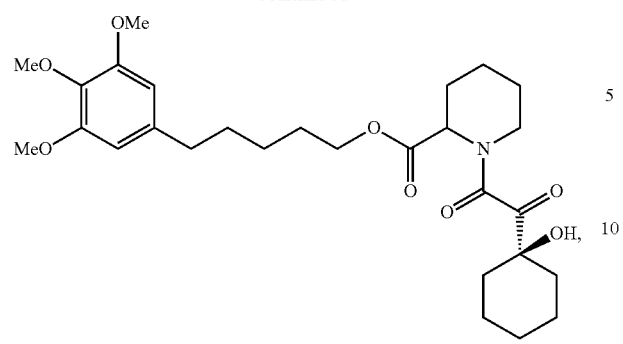
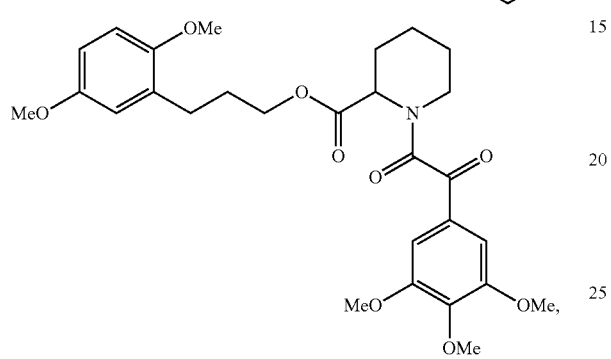
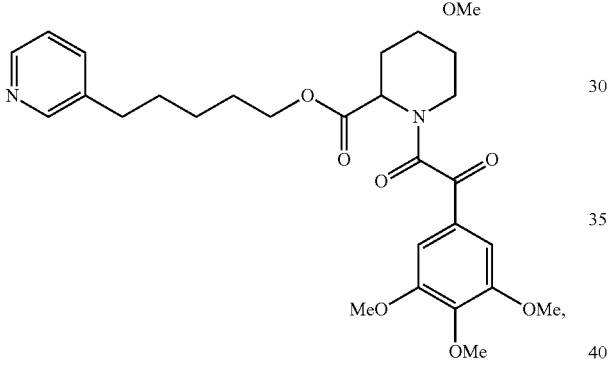
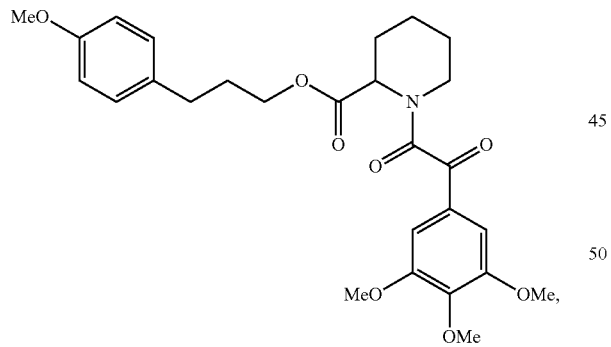
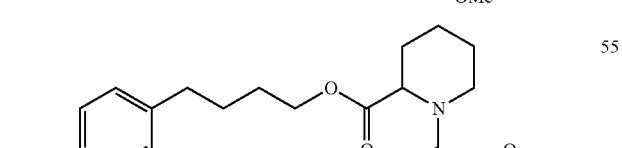
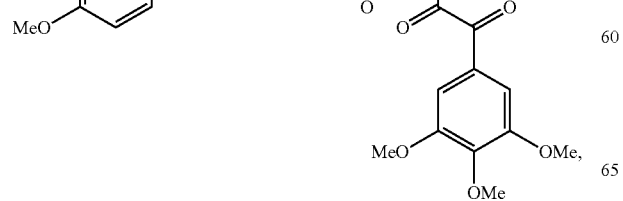
-continued
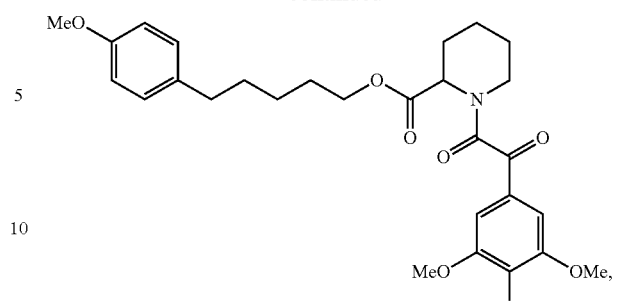
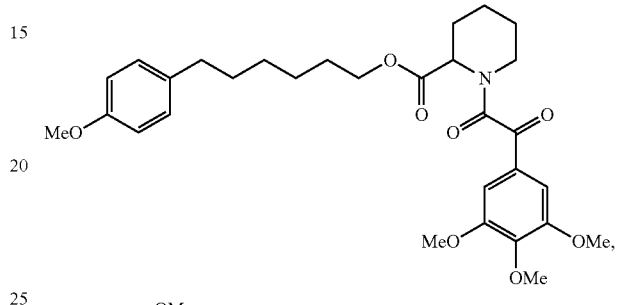
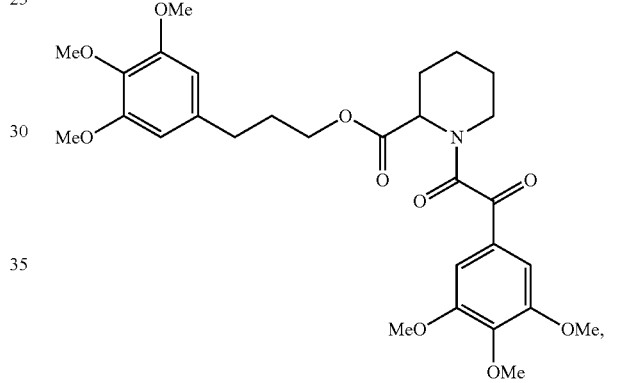
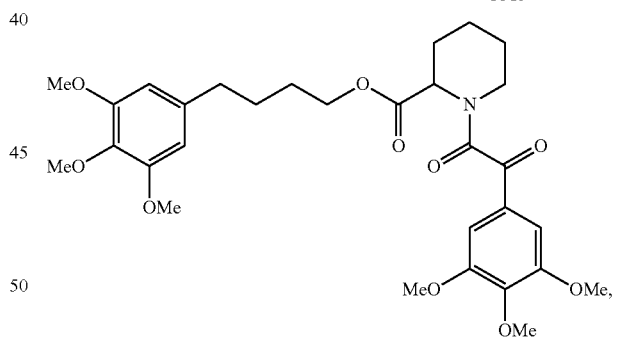
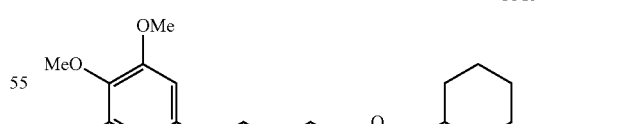
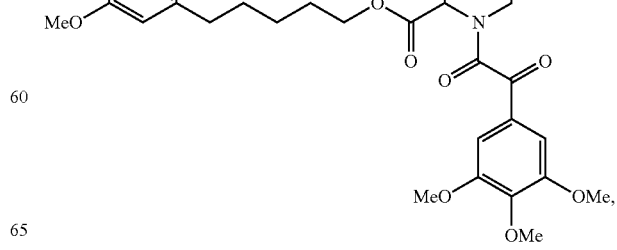

-continued

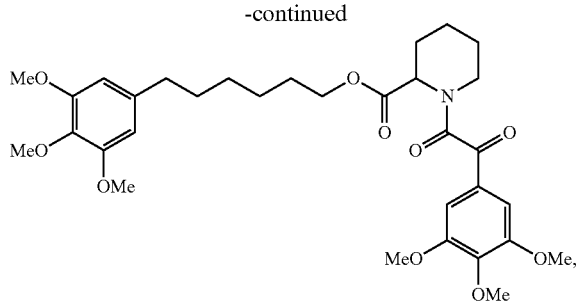

or a pharmaceutically acceptable salt thereof. In some embodiments, the formula is further defined as:

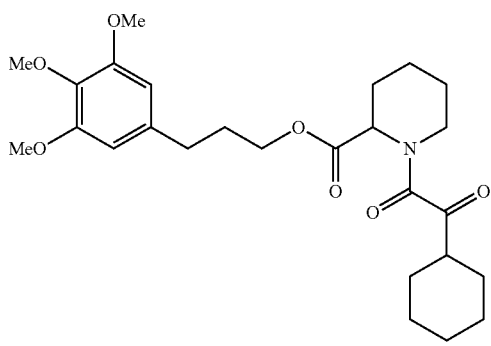 [SMILES: COc1cc(CCCOC(=O)C2CCCCN2C(=O)C(=O)C2CCCCC2)cc(OC)c1OC]

or a pharmaceutically acceptable salt thereof.

In another aspect, the present disclosure provides a compound of the formula:

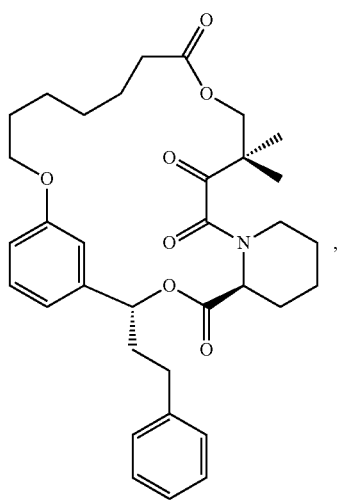

or a pharmaceutically acceptable salt thereof.

In yet another aspect, the present disclosure provides a pharmaceutical composition comprising a compound described in the present disclosure and an excipient. In some embodiments, the pharmaceutical composition is formulated for topical, oral, intraarterial, or intravenous administration.

In another aspect, the present disclosure provides a method of treating a disease comprising administering to a patient in need thereof a therapeutically effective amount of a compound or pharmaceutical composition described in the present disclosure. In some embodiments, the disease is cancer. In some embodiments, the cancer is a solid tumor. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is breast cancer. In some embodiments, the compound or pharmaceutical composition interferes with the assembly of 26S proteasome. In some embodiments, the method further comprises using the compound or pharmaceutical composition in combination with one or more additional therapeutic agents. In some embodiments, the therapeutic agent is chemotherapy, radiotherapy, immunotherapy, or surgery. In some embodiments, the chemotherapy is a proteasome inhibitor. In some embodiments, the proteasome inhibitor is bortezomib.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIGS. 1A-F: (FIG. 1A) Models of probable mechanisms of B1 influence on core particle proteolysis. The cylinder represents the proteasome core particle (CP; 20S). (FIG. 1B) B1 inhibits chymotrypsin-like activity of the core particle with low $IC_{50}$=19 nM. (FIG. 1C) B1 inhibits proteinase activity (degradation of a model substrate casein-BODIPY) of the 26S proteasome assembly with $IC_{50}$=41 nM. (FIG. 1D) B1 synergizes with bortezomib to inhibit chymotrypsin-like activity of the core particle. (FIG. 1E) Atomic force microscopy (AFM) imaging reveals that B1 treatment (100 nM) of the core proteasome results in disturbance in the conformational dynamics of the proteasome a face. Open-gate conformers are represented by white and pink portions of the columns, closed-gate conformers are represented by black and red. Upon the B1 treatment there is a shift toward higher abundance of the open gate conformers (compare columns a and c). However, B1 prevents proteasome from shifting to the majority of open-gate conformers upon treatment with a model peptide substrate (compare columns b and d). (FIG. 1F) Several derivatives of B1 prevent with activation of the core proteasome by Rpt5 tail peptide. In particular, B5, a pentyl-derivative of B1, is at least as efficient as the B1 compound.

FIGS. 2A-E: (FIG. 2A) A model of B1 influence on 26S assembling: B1 blocks binding or the formed 26S is dysfunctional. (FIG. 2B) Top view of a face in 1IRU core particle zoomed into the putative binding site of B1. The groove between α1 and α2 subunits represents the binding site. (FIG. 2C) The compound B1 blocks activation of core proteasome chymotrypsin-like activity with peptides representing anchoring parts of the regulatory particle subunits Rpt2 and Rpt5. The $IC_{50}$ for the blocking is in the range of 2 nM. (FIG. 2D) B1 treatment is exceptionally effective in blocking activation of the core by the Rpt2 tail, even if the tail is present at high, micromolar-range concentrations. (FIG. 2E) B1 at nanomolar concentrations ($IC_{50}$=7.8 nM) interferes with in vitro activation of the core by the purified regulatory particle 19S.

FIGS. 3A-F: (FIG. 3A) The fluorescently labeled B1 derivative, B1-NBD, decorates only the core particle in cell lysates. (FIG. 3B) B1 treatment of the HeLa cells (up to 100 nM shown) does not inhibit mTOR activity, in contrast to rapamycin (Western blot with anti-phosphoS6 antibodies). (FIG. 3C) B1 remains intact in the presence of cell lysate (0.5 mg/ml) or purified CP. RP-HPLC elution profiles for samples incubated for up to 1 h at 37° C. are demonstrated (AcCN gradient 0-100%). (FIG. 3D) Treatment with B1 alone or combined treatment (24 hrs) with bortezomib and B1 is cytotoxic to MCF-7 and MB-231 but not to MCF-10A cells. MDA-MB-231 cells were treated with 40 nM BZ or 160 nM B1 and combination of 20 nM/320 nM BZ/B1. MCF-7 treatment: 40 nM each of BZ, B1 or BZ+B1. MCF-10A: 160 nM each. Assay: trypan blue exclusion test (means of 2 or 3±SD experiments). The viability differences between control (ctrl) and the treatments are statistically significant at p<0.01. Bottom: Cells were treated with increasing concentrations of bortezomib, B1 or bortezomib+B1, in most cases at 1:1 conc. ratio. Combination Index (CI) calculated with the Chou-Talalay formalism falls below 1 for fraction affected >0.3 for MCF-7 and MDA-MB-231 indicating synergism between the drugs. Right: treatment with B1 alone efficiently prevented growth of multiple myeloma RPMI8226 cells. (FIG. 3E) Lysates from B1 (24 hrs, 160 nM) treated MDA-MB-231 cells display accumulation of polyubiquitinated proteins representing substrates which proteasome failed to degrade (Western blotting of cell lysated with specific anti-polyubiquitinated proteins antibodies FK-1). (FIG. 3F) Left: Total proteasome activity in lysates of cultured multiple myeloma cells treated with 50 nM B1 is lower than in control cells treated with vehicle (DMSO). The activity was measured with a model peptide substrate. Right: accordingly, the partition of activities for core particle (20S; low activity) and 26S assembly (high activity) is shifted in the B1-treated cells toward more of the 20S and less of the 26S proteasomes. Activity was measured with a fluorescent model substrate incubated with non-denaturing gels with separated cell lysates.

DESCRIPTION OF ILLUSTRATIVE EMBODIMENTS

Figure 1F:
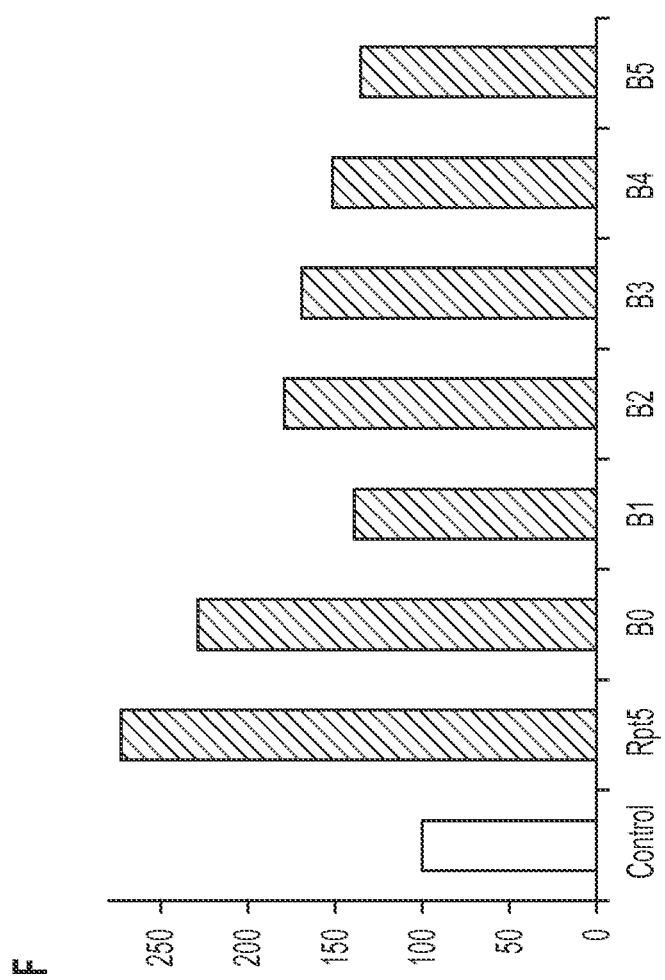

In the search for small molecule, noncompetitive ligands of the proteasome, two general compound classes have been considered: derivatives of natural protein regulators of 20S (Jankowska, et al., 2010) and ligands affecting general protein-protein interactions. The latter approach led to rapamycin (sirolimus): the canonical allosteric macrocycle inducing dimerization of mTOR and FKBP12 (Liang, et al., 1999). Rapamycin in vitro has been found to inhibit two out of three peptidase activities of the 20S and interferes with core catalytic particle-regulatory particle interactions at concentrations disappointingly much higher than those required for mTOR inhibition (Osmulski and Gaczynska, 2013).

As described above, the proteasome represents a broadly accepted target for ligands in the fight against cancer. The present disclosure relates to allosteric ligands which act to inhibit proteasome activity. It also relates to allosteric ligands that increase the effectiveness of proteasome competitive inhibitors. In some embodiments, the allosteric ligands could bind to proteasome leading to enhanced efficacy of the competitive proteasome in the treatment of cancer. Furthermore, the allosteric ligands for proteasome of the present disclosure may act on solid tumors to increase the efficacy of the proteasome treatment. In some embodiments, the allosteric ligands describe herein could assist in the fight against drug resistant cancer by modulating the activity of the proteasome inhibitors, e.g., in blood cancers.

In an attempt to separate the mTOR and proteasome related functions, seco-rapamycin, a linear first metabolite of rapamycin that cannot bind the mTOR (Ma and Blenis, 2009) but affects the proteasome function similarly to rapamycin, was found. Molecular modeling pointed at the grooves between α subunits as potential binding sites for rapamycin and its metabolite. The compound, B1, interferes with 26S assembling and influences proteasome activities at nanomolar concentrations while not affecting mTOR pathway. Unexpectedly, B1 increases affinity of core particle toward bortezomib leading to strong cytotoxic effects on cultured breast cancer cells, which are poorly responsive to bortezomib.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⚌" represents a single bond or a double bond. Thus, for example, the structure

includes the structures

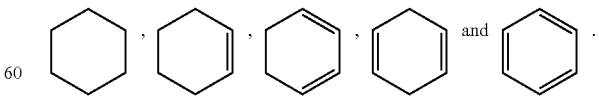

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in unambiguously identifying a point of attachment. The symbol "◀━" means a single bond where the group attached to the thick end of the wedge is "out of the page." The symbol "▪▪▫▫▫" means a single bond where the group attached to the thick end of the wedge is "into the page". The symbol "∿∿" means a single bond where the conformation (e.g., either R or S) or the geometry is undefined (e.g., either E or Z). Similarly, the covalent bond symbol "—", when connecting stereogenic atom, does not indicate any preferred stereochemistry, it does cover all stereoisomers, including the "◀━" and "▪▪▫▫▫" forms.

Any undefined valency on an atom of a structure shown in this application implicitly represents a hydrogen atom bonded to the atom. A bold dot on a carbon atom indicates that the hydrogen attached to that carbon is oriented out of the plane of the paper. When a group "R" is depicted as a "floating group" on a ring system, for example, in the formula:

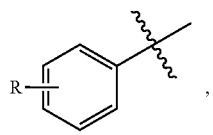

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

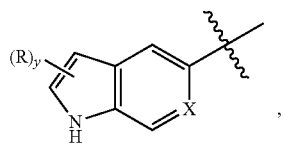

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH₂, =CH(CH₂CH₃), and =C(CH₃)₂. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CHC₆H₅. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. When alkynyl is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

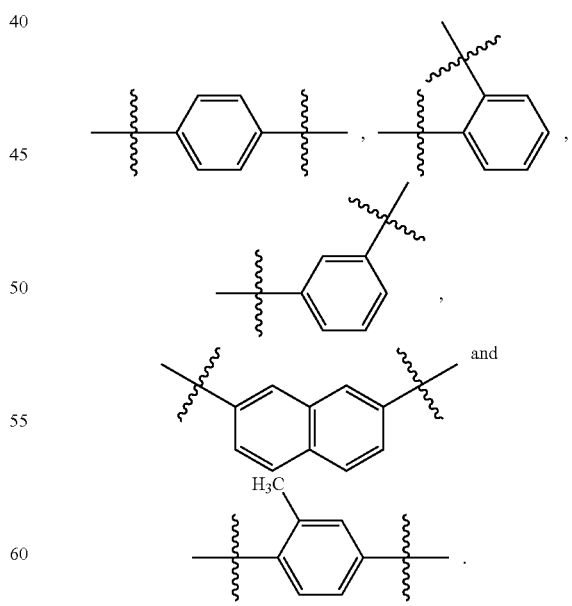

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)

CH₃, —NHCH₃, —NHCH₂CH₃, —N(CH₃)₂, —C(O)NH₂, —OC(O)CH₃, or —S(O)₂NH₂. An "arene" refers to the compound HR, wherein R is aryl. Benzene and toluene are non-limiting examples of arenes.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

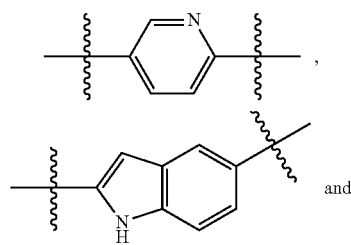

and

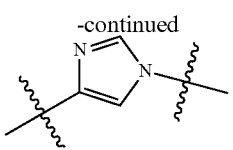

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂, or —C(O)OC (CH₃)₃ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH (CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃

(ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl, O-alkanediyl-O—, or -alkanediyl-O-alkanediyl-. The term "alkylthio" and "acylthio" when used without the "substituted" modifier refers to the group SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group. Similarly, the term "ether" corresponds to an alkane, as defined above, wherein at least one of the hydrogen atoms has been replaced with an alkoxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which causes 50% inhibition of a given process. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Allosteric Ligands of Proteasomes and Synthetic Methods Thereof

In the present invention, attempts to synthesize novel allosteric ligands for proteasomes are described. The novel allosteric ligands for proteasome described in this disclosure can be prepared according to the methods described in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The novel allosteric ligands for proteasomes described in this disclosure may contain one or more asymmetricallysubstituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The allosteric ligands for proteasome may occur as racemates and racemic mixtures, single enantiomers, diastereomeric mixtures and individual diastereomers. In some embodiments, a single diastereomer is obtained. The chiral centers of the present invention can have the S or the R configuration.

In addition, atoms making up the allosteric ligands of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of the novel allosteric ligands for proteasome may be replaced by a sulfur or selenium atom(s).

The novel allosteric ligands for proteasome may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical advantages over, compounds known in the prior art for use in the indications stated herein.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

III. Hyperproliferative Diseases

While hyperproliferative diseases can be associated with any disease which causes a cell to begin to reproduce uncontrollably, the prototypical example is cancer. One of the key elements of cancer is that the cell's normal apoptotic cycle is interrupted and thus agents that lead to apoptosis of the cell are important therapeutic agents for treating these diseases. In this disclosure, the allosteric ligands have been shown to lead to decreased cell counts and as such can potentially be used to treat a variety of types of cancer lines. As such, the compounds described in the disclosure may be effective in treating cancers which form a solid tumor. In some embodiments, those cancers include breast cancer. In other embodiments, the compounds described in the disclosure may be used to modulate the drug resistance of a solid tumor or a cancer of the blood. In various aspects, it is anticipated that the compounds of the present invention may be used to treat virtually any malignancy.

Cancer cells that may be treated with the compounds according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone;

ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

IV. Allosteric Inhibitors of Proteasome

In some embodiments, the compounds of the present disclosure act to modulate the efficacy of a drug in treating a solid a tumor. Without being bound by theory, the compounds act as allosteric ligands which regulate binding of another drug to proteasome which leads to changes in that drugs effectiveness in treating the tumor. In some embodiments, the compound described by the formula:

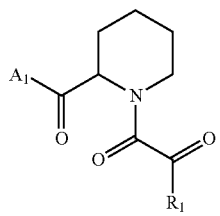

(I)

wherein: $A_1$ is hydroxy, amino, or

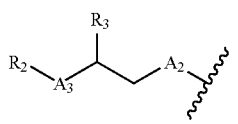

wherein: $A_2$ is —O— or —$NR_6$— wherein $R_6$ is hydrogen, alkyl$_{(C \leq 6)}$ or substituted alkyl$_{(C \leq 6)}$; $A_3$ is alkanediyl$_{(C \leq 6)}$, alkenediyl$_{(C \leq 6)}$, or a substituted version of either of these groups; $R_2$ is

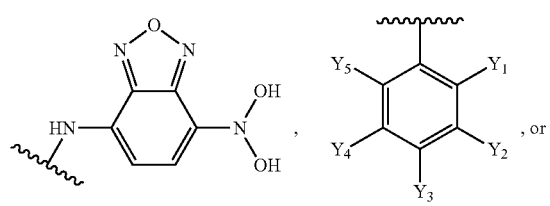

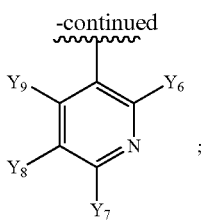

wherein: $Y_1$, $Y_2$, $Y_3$, $Y_4$, $Y_5$, $Y_6$, $Y_7$, $Y_8$, and $Y_9$ are each independently hydrogen, hydroxy, phosphate, halo, alkyl$_{(C \leq 12)}$, alkoxy$_{(C \leq 12)}$, acyloxy$_{(C \leq 12)}$, heteroaryl$_{(C \leq 12)}$, acyl$_{(C \leq 12)}$, alkylamino$_{(C \leq 12)}$, dialkylamino$_{(C \leq 12)}$, or a substituted version of any of these groups; $R_3$ is hydrogen, alkyl$_{(C \leq 8)}$, or a substituted alkyl$_{(C \leq 8)}$; and $R_1$ is

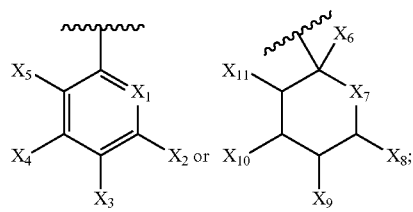

wherein: $X_1$ is O, N, or $CR_4$; $X_2$, $X_3$, $X_4$, $X_5$, and $R_4$ are each independently hydrogen, hydroxy, phosphate, halo, alkyl$_{(C \leq 12)}$, alkoxy$_{(C \leq 12)}$, acyloxy$_{(C \leq 12)}$, heteroaryl$_{(C \leq 12)}$, acyl$_{(C \leq 12)}$, alkylamino$_{(C \leq 12)}$, dialkylamino$_{(C \leq 12)}$, or a substituted version of any of these groups; $X_6$ is hydrogen or hydroxy; $X_2$ is O, NH, or $C(R_5)_2$; $X_8$, $X_9$, $X_{10}$, $X_{11}$, and $R_5$ are each independently hydrogen, hydroxy, phosphate, halo, alkyl$_{(C \leq 12)}$, alkoxy$_{(C \leq 12)}$, acyloxy$_{(C \leq 12)}$, heteroaryl$_{(C \leq 12)}$, acyl$_{(C \leq 12)}$, alkylamino$_{(C \leq 12)}$, dialkylamino$_{(C \leq 12)}$, or a substituted version of any of these groups; or a pharmaceutically acceptable salt thereof.

In some embodiments, the compounds that may act as allosteric ligands for proteasome include compounds of the formula:

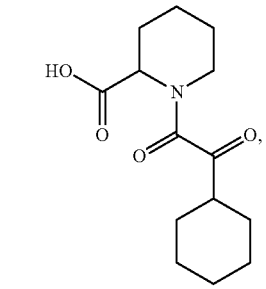

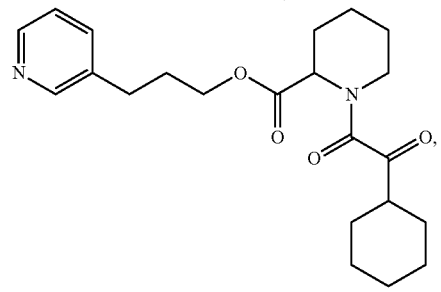

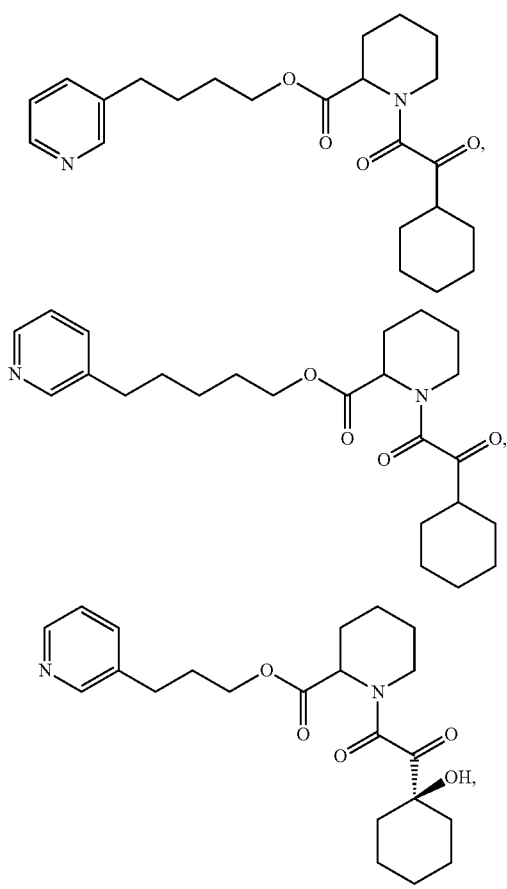
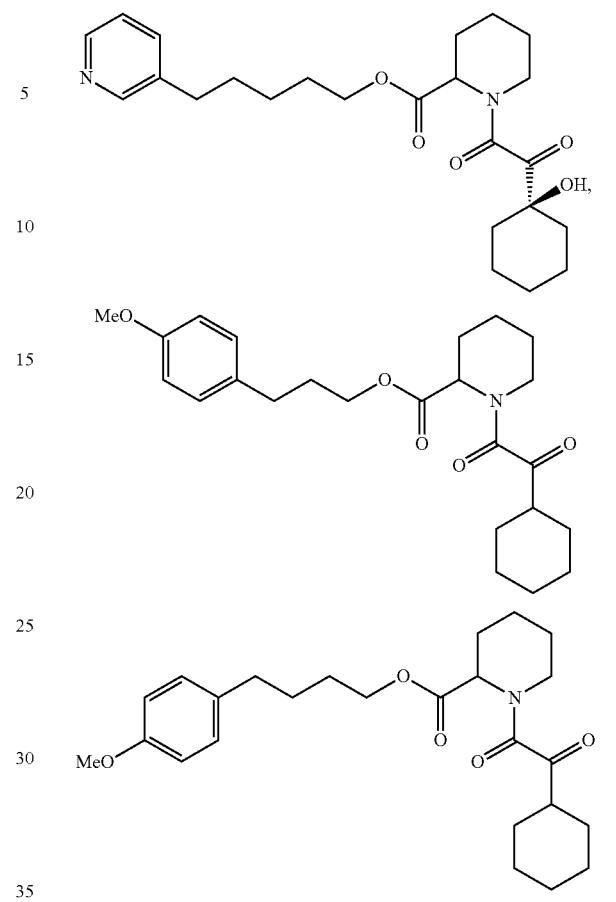
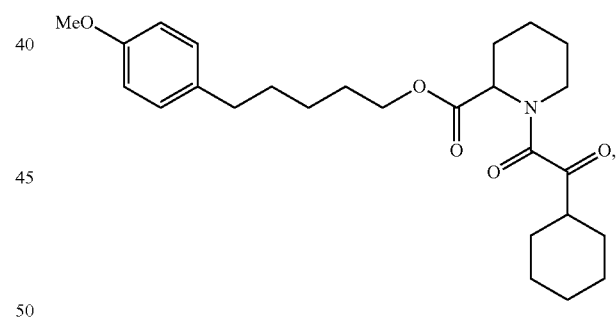
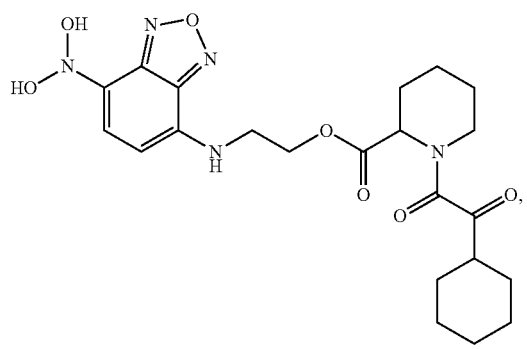

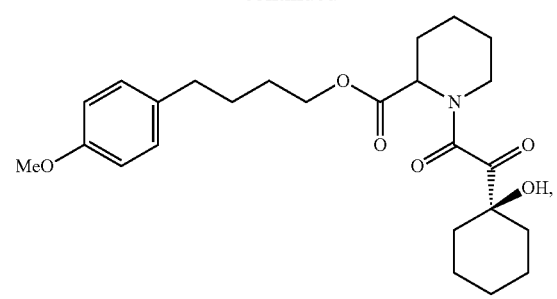
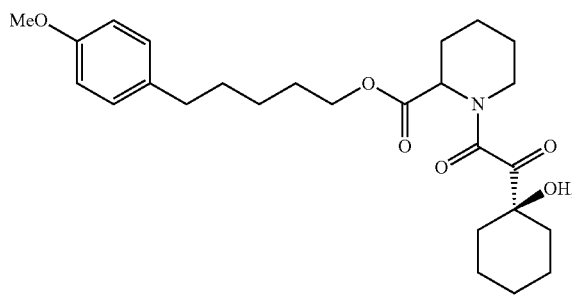
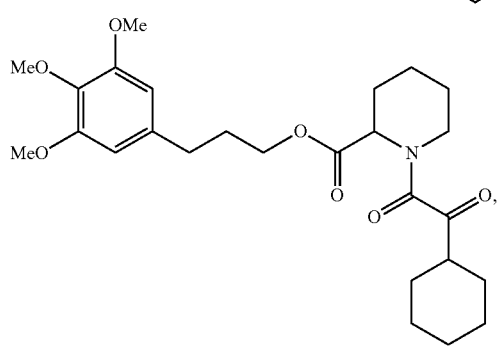
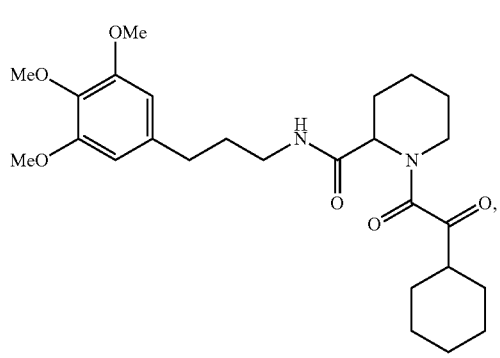
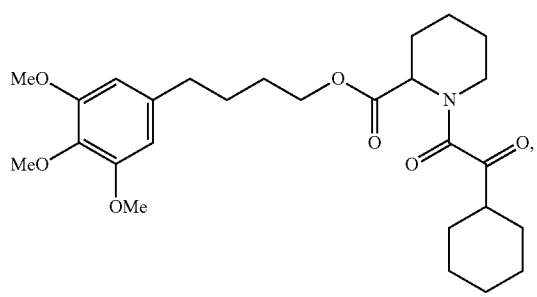
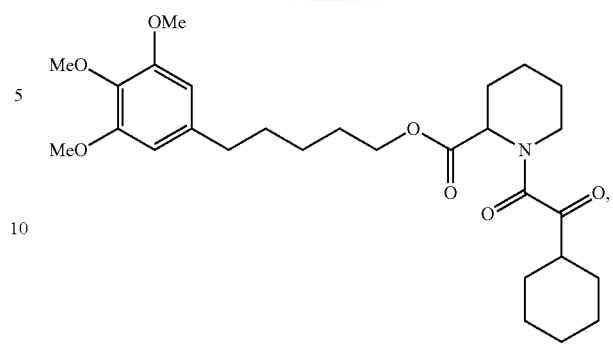
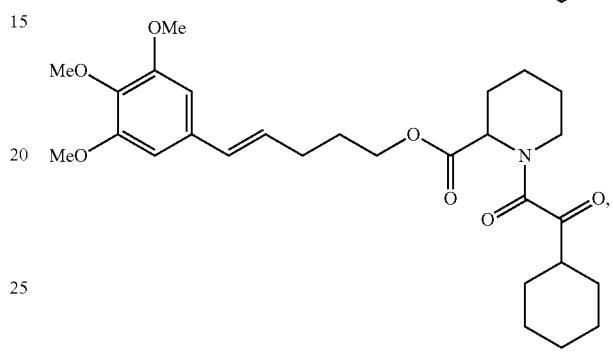
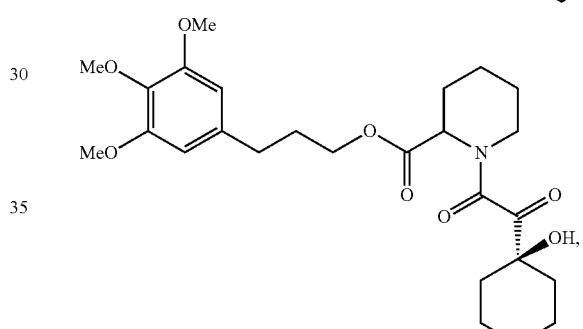
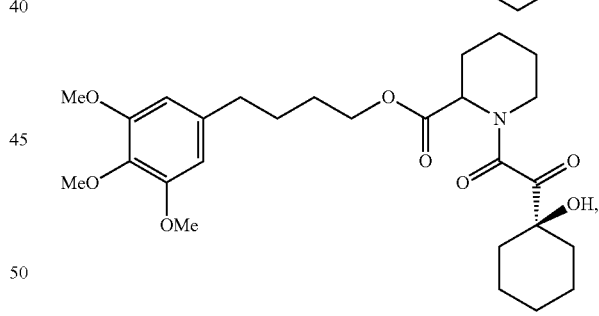
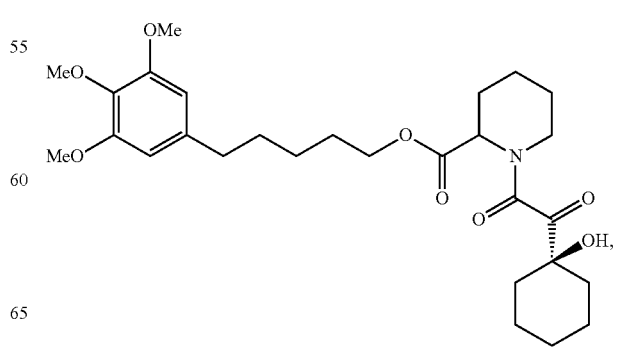

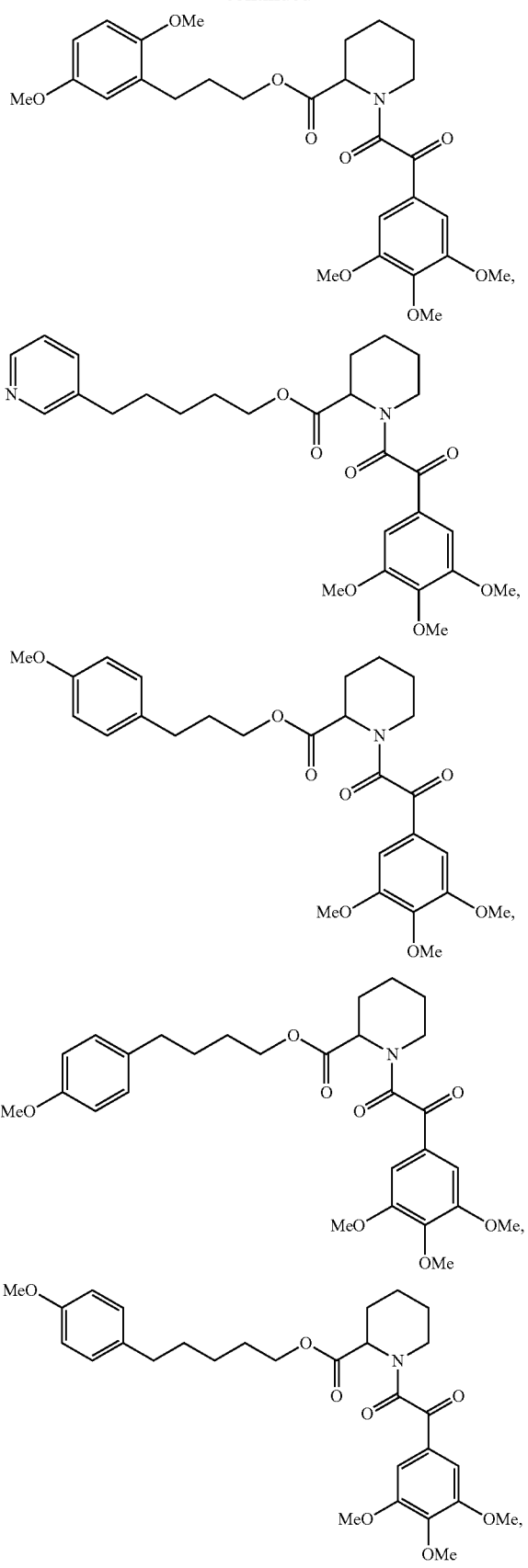
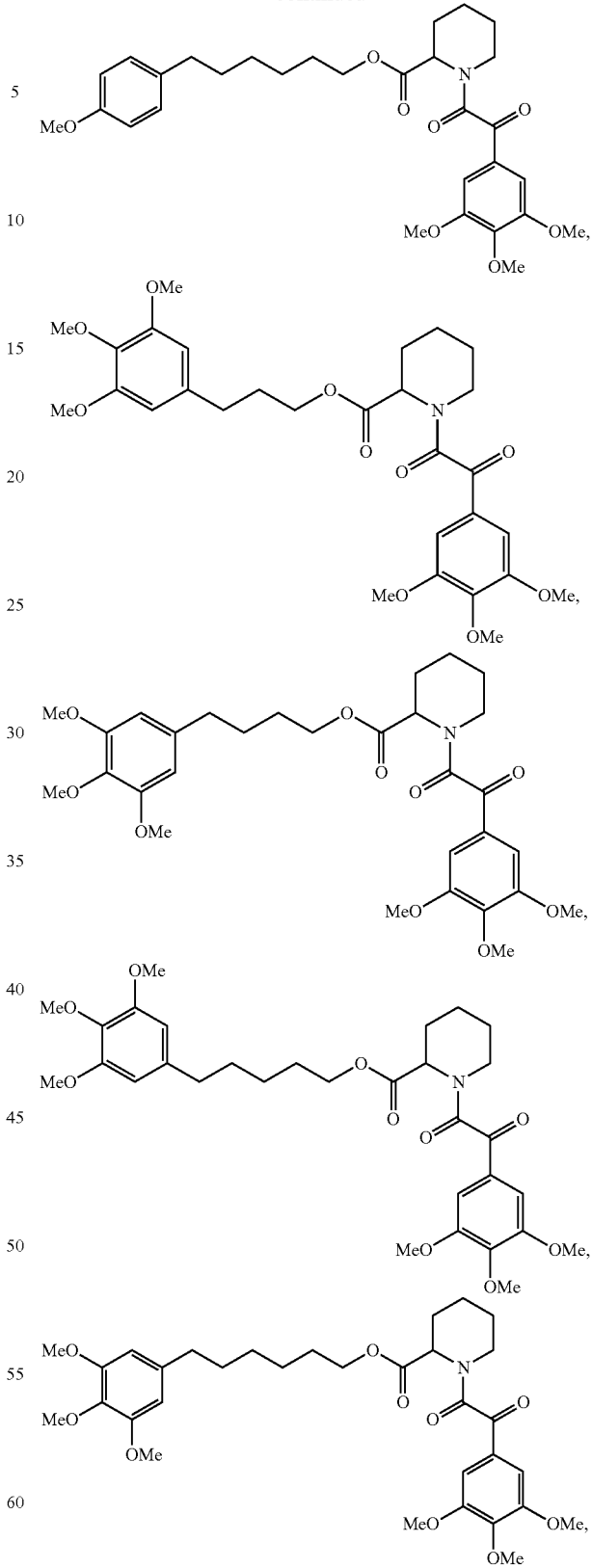
or a pharmaceutically acceptable salt thereof. In some embodiments, the compound is preferentially of the formula:

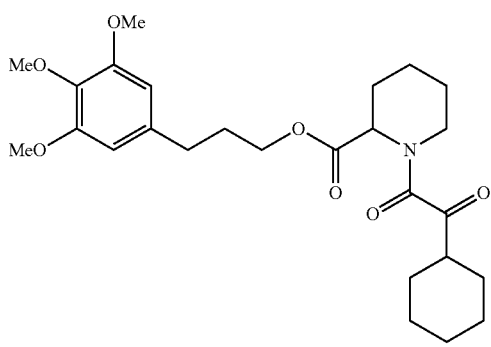 [SMILES: COc1cc(CCCOC(=O)C2CCCCN2C(=O)C(=O)C2CCCCC2)cc(OC)c1OC]

or a pharmaceutically acceptable salt thereof. In some embodiments, the compound has a formula:

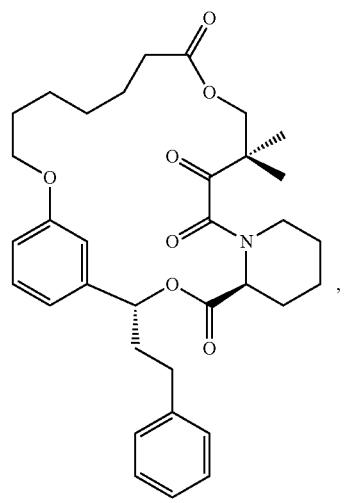

or a pharmaceutically acceptable salt thereof. The above described compounds are the preferred embodiment of the compounds of the disclosure and can be prepared as described in this application or through the methods described in the art without undue experimentation. In some aspects of the present disclosure, the compounds may also be references by their name, an abbreviation or other property. The following table provides appropriate names and abbreviations for some of the compounds described in the present disclosure.

TABLE 1

| Compounds of the Present Disclosure | |
|---|---|
| Abbreviation | Compound |
| B0 | |

TABLE 1-continued

| Compounds of the Present Disclosure | |
|---|---|
| Abbreviation | Compound |
| B1 | |
| B2 | |
| B3 | |
| B4 | |

TABLE 1-continued

Compounds of the Present Disclosure

| Abbreviation | Compound |
|---|---|
| B5 | 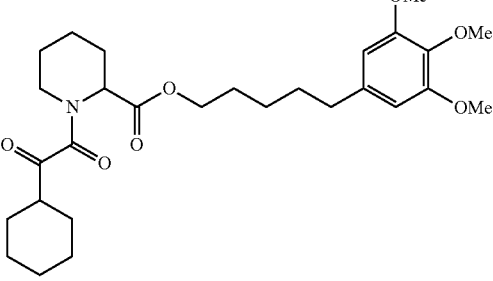 |

V. Pharmaceutical Formulations and Routes of Administration

For administration to a mammal in need of such treatment, the allosteric ligands for proteasome in a therapeutically effective amount are ordinarily combined with one or more excipients appropriate to the indicated route of administration. The allosteric ligands for proteasome may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the allosteric ligands may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The allosteric ligands for proteasome may be administered by a variety of methods, e.g., orally or by injection (e.g. subcutaneous, intravenous, intraperitoneal, etc.). Depending on the route of administration, the novel allosteric ligands may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the allosteric ligands for proteasome with, or co-administer the novel allosteric ligands for proteasome with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The allosteric ligands for proteasome may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion are also envisioned. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the allosteric ligands for proteasome in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The allosteric ligands for proteasome can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the allosteric ligands may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the allosteric ligands for proteasome in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of the novel allosteric ligands for proteasome calculated to produce the desired therapeutic effect in association with the required pharmaceutical carrier. The specification for the dosage unit forms of the invention are dictated by and directly dependent on (a) the unique characteristics of the allosteric ligands for proteasome described in this invention and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The allosteric ligands for proteasome describe in this disclosure are administered at a therapeutically effective dosage sufficient to treat a condition associated with a condition in a patient. For example, the efficacy of the allosteric ligands for proteasome can be evaluated in an animal model system that may be predictive of efficacy in treating the disease in humans, such as the model systems shown in the examples and drawings.

The actual dosage amount of the allosteric ligands for proteasome of the present disclosure or composition comprising the inhibitors of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 1 mg/kg to about 50 mg/kg, in one or more dose administrations daily, for one or several days (depending of course of the mode of administration and the factors discussed above). In some particular embodiments, the amount is less than 5,000 mg per day with a range of 10 mg to 4500 mg per day.

The effective amount may be less than 10 mg/kg/day, less than 50 mg/kg/day, less than 100 mg/kg/day, less than 250 mg/kg/day. It may alternatively be in the range of 1 mg/kg/day to 250 mg/kg/day.

In other non-limiting examples, a dose may also comprise from about 0.1 mg/kg/body weight, about 1 mg/kg/body weight, about 10 g/kg/body weight, about 50 g/kg/body weight, or more per administration, and any range derivable therein. In non-limiting examples of a derivable range from the numbers listed herein, a range of about 1 mg/kg/body weight to about 50 mg/kg/body weight, about 5 g/kg/body weight to about 10 g/kg/body weight, etc., can be administered, based on the numbers described above.

In certain embodiments, a pharmaceutical composition of the present disclosure may comprise, for example, at least about 0.1% of an inhibitor described in the present disclosure. In other embodiments, the compound of the present disclosure may comprise between about 0.25% to about 75% of the weight of the unit, or between about 25% to about 60%, or between about 1% to about 10%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The allosteric ligands may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat. In some embodiments, the allosteric ligands of proteasome are taken before the onset of the tumor as a prophylaxis measure. In other embodiments, the allosteric ligands of proteasome are taken as a treatment option for use as an antiproliferative agent.

VI. Combination Therapy

In addition to being used as a monotherapy, the allosteric ligands of proteasomes described in the present invention may also find use in combination therapies. Effective combination therapy may be achieved with a single composition or pharmacological formulation that includes both agents, or with two distinct compositions or formulations, administered at the same time, wherein one composition includes an allosteric ligand of proteasome, and the other includes the second agent(s). The other therapeutic modality may be administered before, concurrently with, or following administration of the allosteric ligands of proteasome. The therapy using the allosteric ligands of proteasome may precede or follow administration of the other agent(s) by intervals ranging from minutes to weeks. In embodiments where the other agent and the compounds of the present disclosure which act as allosteric ligands of proteasome are administered separately, one would generally ensure that a significant period of time did not expire between the time of each delivery, such that each agent would still be able to exert an advantageously combined effect. In such instances, it is contemplated that one would typically administer the allosteric ligands of proteasome and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a novel allosteric ligand of proteasome, or the other agent will be desired. In this regard, various combinations may be employed. By way of illustration, where the novel allosteric ligand of proteasomes is "A" and the other agent is "B", the following permutations based on 3 and 4 total administrations are exemplary:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated. Non-limiting examples of pharmacological agents that may be used in the present invention include any pharmacological agent known to be of benefit in the treatment of a cancer or hyperproliferative disorder or disease. In some embodiments, combinations of the allosteric ligands of proteasome with a cancer targeting immunotherapy, radiotherapy, chemotherapy, or surgery are contemplated. Also contemplated is a combination of the allosteric ligands of proteasome with more than one of the above mentioned methods including more than one type of a specific therapy. In some embodiments, the compounds of the present invention are given in conjunction with the chemotherapeutic agent, bortezomib. In some embodiments, the compounds of the present invention are given in conjunction with the chemotherapeutic agent, PR-171. In some embodiments, it is contemplated that the immunotherapy is a monoclonal antibody which targets HER2/neu such trastuzumab (Herceptin®), alemtuzumab (Campath®), bevacizumab (Avastin®), cetuximab (Eribitux®), and panitumumab (Vectibix®) or conjugated antibodies such as ibritumomab tiuxetan (Zevalin®), tositumomab (Bexxar®), brentuximab vedotin (Adcetris®), ado-trastuzumab emtansine (Kadcyla™), or denileukin dititox (Ontak®) as well as immune cell targeting antibodies such as ipilimumab (Yervoy®), tremelimumab, anti-PD-1, anti-4-1-BB, anti-GITR, anti-TIM3, anti-LAG-3, anti-TIGIT, anti-CTLA-4, or anti-LIGHT. Furthermore, in some embodiments, the allosteric ligands of proteasome are envisioned to be used in combination therapies with dendritic cell-based immunotherapies such as Sipuleucel-T (Provenge®) or adoptive T-cell immunotherapies.

Furthermore, it is contemplated that the allosteric ligands of proteasome are used in combination with a chemotherapeutic agent such as PR-171 (Kyprolis®), bortezomib (Velcade®), anthracyclines, taxanes, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, oxaliplatin, BRAF inhibitors, and TGF-beta inhibitors. In some embodiments, the combination therapy is designed to target a cancer such as those listed above. In the preferred embodiments, the cancer the combination therapy is designed to treat is breast cancer or another solid tumor. In other embodiments, the cancer combination therapy is used to treat blood cancers by modulating their drug resistance.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Rapamycin Pharmacophore and Proteasome Inhibitors

The rapamycin molecule contains two distinct pharmacophores responsible for its potential to dimerize mTOR with FKBP12 and allosterically inhibit mTOR. This peculiar property inspired tests whether rapamycin and related pharmacophores also participates in protein-protein interactions regulating catalytic performance of proteasome. Recently, this disclosure provides that:

1. Rapamycin and related pharmacophores is a noncompetitive inhibitor of proteasome ChT-L and PGPH peptidase activities.
2. Only analogs of rapamycin are proteasome inhibitors, whereas competitive inhibitors of mTOR kinase structurally unrelated to rapamycin do not inhibit proteasome.
3. Rapamycin and related pharmacophores binding to CP increases its affinity to competitive inhibitors such as Bortezomib.
4. Rapamycin and related pharmacophores destabilizes the 26S proteasome impeding the intracellular activity of 26S proteasome and thus the performance of ubiquitin-proteasome pathway.
5. Binding of rapamycin and related pharmacophores to the core proteasome renders the specific docking sites inaccessible for 19S particle what leads to inhibition of the 26S proteasome assembling.
6. Rapamycin and related pharmacophores induces conformational changes at the α face detectable by AFM imaging and crosslinking/MS. The results support the concept that the α face provides binding domain(s) for rapamycin.

Additionally, HeLa cells treated with pharmacologically relevant doses of rapamycin and related pharmacophores have been found to have compromised stability of 26S proteasomes. Moreover, the drugs targeting the mTOR and UBP pathways inflict much stronger toxicity in combination than when used individually.

Example 2—Molecular Mechanism Between Inhibitor B1 and Competitive Inhibitors

The novel proteasome inhibitor, B1, inhibits chymotrypsin-like and post-glutamyl peptidases of the core particle via allosteric processes (FIG. 1A-B) with noncompetitive mechanism. The kinetic parameters of the inhibition of the chymotrypsin-like peptidase are: $K_M$=91 microM, $V_{max}$=0.195 nanomoles of product per mg of proteasome per second. Also, it inhibits the proteinase activity of the 26S assembly (FIG. 1C). A synergistic in vitro effect between compound B1 and bortezomib in inhibition of the chymotrypsin-like active site is shown in FIG. 1D. AFM imaging revealed the unusually high content of open-gate conformers in the core particle treated with B1, a feature shared with seco-rapamycin and rapamycin (FIG. 1E). The partition of the conformers was insensitive to treatment with substrates. Since gate dynamics of the core particle is essential for catalysis (Osmulski, et al., 2009), the disruption of gate movements is believed to participate in the inhibitory mechanism (FIGS. 1A, E). B1 possesses a three-carbon (propyl) chain linking cyclic components. Modification to the chain (B2 compound), addition of the fluorescent tag to the B1 lead (B3 compound) or extending the length of chain to five-carbon (pentyl; B4 and B5 compounds) does not erase the inhibitory properties toward the core proteasome. Moreover, the B5 compound is preventing activation of the core proteasome by Rpt5 tail peptide at least as good as the parent B1 compound (FIG. 1F).

Example 3—Molecular Mechanism Between Inhibitor B1 and the Core Particle and the Regulatory Particle The compound B1 has been observed to prevent activation of the core particle by the regulatory particle and the HbYX peptides derived from Rpt5 and, in particular, Rpt2 (Rpt5 and Rpt2 tails; FIGS. 2A-D). Molecular modeling indicates that the compound B1 binds in one or more grooves between the a subunits of the catalytic core (FIGS. 2A-B). The grooves are utilized by Rpt2, Rpt3 and Rpt5 subunits that anchor the regulatory particle to the core particle (Lander, et al., 2009). The anchoring C-terminal tails of Rpt2 and Rpt5 subunits are responsible for core particle gate opening and activation (Lander, et al., 2009). Activation of the core by both Rpt2 and Rpt5 tails is affected by B1 (FIG. 2C). The groove accommodating the C-terminal tail of Rpt2 subunit may be a primary docking place for B1, or B1 may allosterically affect binding of Rpt2 C-terminal tail with an exceptionally high efficiency (FIG. 2D). In vitro reconstruction of the 26S proteasome assembly from the core particle (20S) and regulatory particle (19S) components is attenuated by the treatment with B1 (FIG. 2E).

Example 4—Anti-Cancer Actions of B1 In Celiac

The proteasome appears to be the exclusive target for B1 (FIGS. 3A-E). A fluorescent version of B1, B1-NBD (trimethoxyphenyl group substituted with nitrobenzofurazan) was prepared. In vitro B1-NBD and B1 have been shown to affect the core particle in a similar way. Lysates and cytosolic extracts prepared from Mcf7 breast carcinoma and Mcf10A noncancerous control cells were treated with B1-NBD and fractionated with nondenaturing 4% and 4%-20% gradient PAGE. The band identified by zymogram as the core particle in the low-density gel was the sole fluorescing species (FIGS. 3A-D).

The in vitro effects of the compound B1 are also detectable in cell lysates (FIGS. 3A-E). The total chymotrypsin-like activity of the proteasome in the Mcf7 and Mcf10A lysates was measured. The inhibition by B1 and the synergy between B1 and bortezomib was well pronounced in the Mcf7 lysate (FIGS. 3A-D). Consistently, mTOR does not appear to be affected by the treatment of cultured HeLa cells with B1 (FIG. 3B). Also, B1 appears to be stable in the presence of the whole cell lysate or the purified core particle (FIG. 3C).

The effects of 24-96 hours treatment with B1, bortezomib, and their combination on HeLa.S3, RPMI8226, Mcf7, MDA-MB-231 and Mcf10A were tested. The cytotoxicity with the LIVE/DEAD Viability-Cytotoxicity Kit (Invitrogen) or with trypan blue exclusion assay was analyzed. All cultured cancer cells tested, including poor bortezomib responders Mcf7 and MDA-MB-231 were sensitive to the treatment with B1 alone and in combination with bortezomib, with a strong synergy between the two inhibitors. Multiple myeloma cultured cells were particularly sensitive to the treatment with B1, with $IC_{50}=59$ nM (FIG. 3D). The non-cancerous Mcf10A cells were refractory to the treatment (FIG. 3D). Consistently with proposed actions of B1 as the agent interfering with 26S assembly and/or stability, the lysates prepared from B1-treated cells contained excess of non-degraded proteasome substrates (FIG. 3E). The total proteasome activities were lower in B1-treated cells and the partition between 20S and 26S assemblies was shifted toward less of the full 26S assemblies (FIG. 3F).

The activities and content of the proteasome assemblies in extracts from a panel of six diverse breast cancer and two control breast cell lines were measured and analyzed. In the case of two cancer-control pairs, the Mcf7 (luminal A)-Mcf10A and HS 578 T (basal B, triple negative)-HS 578Bst, strong upregulation of the proteasome content in breast cancers as compared with controls was observed for both pairs. In addition, the chymotrypsin-like activity in Mcf7 cell extracts was several-fold higher than in Mcf10A control.

The compound B1 was found to be highly cytotoxic to cancer cells at concentrations lower than those the inventors used in vitro. The exceptionally strong effects of B1 on breast cancer cells may results from the intrinsic properties of the proteasome and/or the intracellular milieu.

Example 5—Synthesis of Compounds

Synthesis of B0 and B1

Methyl pipecolinate 1 was condensed with chlorooxoacetate and triethyl amine (TEA) to produce oxamate 2 (89% yield). 2 was treated with cyclohexyl magnesium bromide in tetrahydrofuran (THF) forming glyoxylate 3 (58% yield HPLC). Carboxylic acid 4 was produced after ester hydrolysis with lithium hydroxide (63% yield). This compound was named B0 and used as a precursor for synthesis of other B series compounds. The desired 3,4,5-trimethoxyphenpropyl side chain 6 was prepared by reduction of 3,4,5-trimethoxycinnamic acid 5 with lithium aluminum hydride (LAH, 57% yield).

The corresponding derivatives of B1 with modified length of the aliphatic chain were produced with analogs of 3,4,5-trimethoxy acids.

1,3-dicyclohexylcarbodiimide (DCC) was used to couple the acid 4 with the alcohol 6 to form B1 that was further purified with flash chromatography. B1 was obtained with 65% yield as an off-white oil in >96% purity.

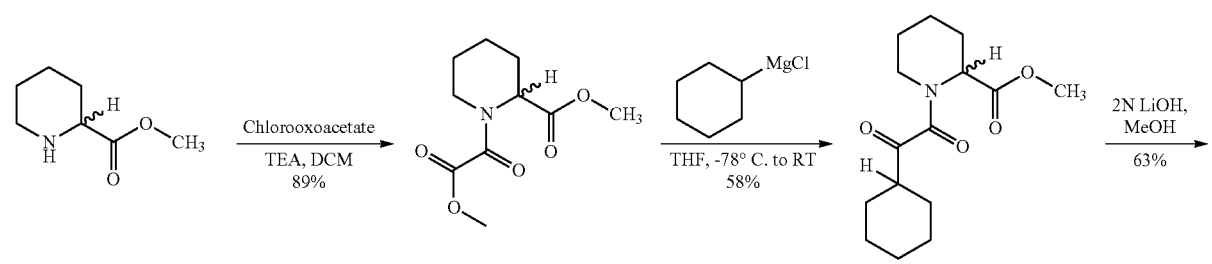

-continued

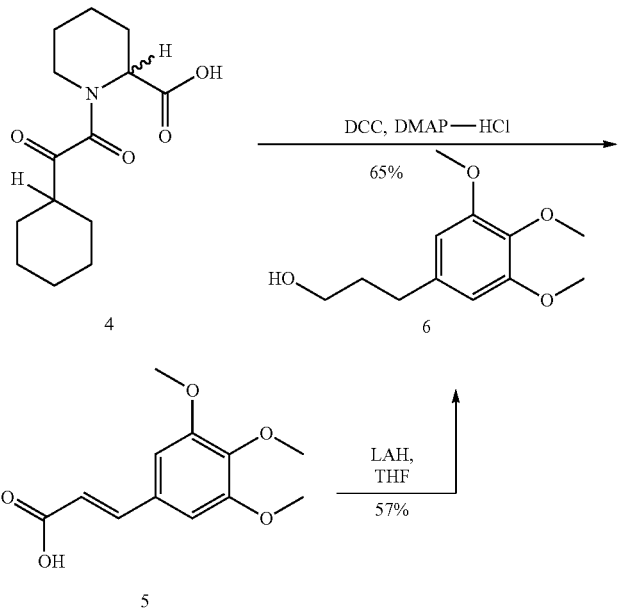

NMR Data: $^1$H NMR 400 MHz (4:1 mixture of cis-trans amide rotamers) (CDCl$_3$) δ 7.26 (CDCl$_3$) 6.41 (s, 2H), 5.28 (d, 1H, J=5.5 Hz), 4.49 (m, 1H), 4.20 (m, 2H), 3.86 (s, 6H), 3.83 (s, 3H), 3.57 (br d, 1H, J=13.3 Hz), 3.23 (td, 1H, J=13.2 Hz, 3.0 Hz), 2.87-3.06 (two M, 1H) 2.64 (t, 2H, J=8.0 Hz), 2.26-2.33 (two d, 1H, J=13.6 Hz), 1.66-2.06 (m, 4H), 1.63-1.84 (m, 6H), 1.12-1.58 (m, 8H)

$^{13}$C NMR (CDCl$_3$) (4:1 mixture of cis-trans amide rotamers) δ (ppm) 203.5, 170.5, 170.3, 167.8, 166.7, 136.6, 136.5, 136.2, 105.3, 77.3-76.7 (CDCl$_3$) 64.8, 64.7, 60.8, 56.3, 56.0, 51.6, 47.0, 46.7, 43.9, 39.4, 32.4, 32.3, 30.3, 30.2, 27.5, 27.3, 26.80, 25.80, 26.76, 26.35, 25.74, 25.70, 25.46, 25.36, 25.21, 25.19, 25.00, 24.42, 21.09, 20.87

LC Mass Spectroscopy: Observed m/z 476.3 (M+H). Observed 448.3, 338.2 (m-C$_8$H$_{10}$O$_2$), 250.2, 207.2

B0

Chemical Name: 1-(2-cyclohexyl-2-oxoacetyl)piperidine-3-carboxylic acid Formula: C$_{14}$H$_{21}$NO$_3$
MW: 267.32
Appearance: White Solid
Soluble in: DMSO, CDCl$_3$ Synthesis of B2

Chemical Name: 3-(3,4,5-trimethoxyphenyl)propyl 1-(2-cyclohexyl-2-oxoacetyl)piperidine-2-amide)
Formula: C$_{26}$H$_{38}$N$_2$O$_6$
MW: 474.59
Appearance: Off-white oil
Soluble in: DMSO, CDCl$_3$
NMR Data
$^1$H NMR 400 MHz (1:1 mixture of cis-trans amide rotamers) (CDCl$_3$) δ 6.78 (t, 1H), 6.39 (s, 2H), 6.38 (s, 2H), 6.01 (t, 1H), 5.04 (d, 2H), 4.46 (m, 1H), 4.06 (d, 1H), 3.83 (overlapping s, 12H), 3.78 (s, 6H), 3.48 (m, 1H), 3.29-3.40 (m, 2H), 3.17-3.29 (m, 2H), 3.08-3.16 (dt, 1H), 2.82-3.08 (tt, 1H), 2.85-2.93 (tt, 1H), 2.51-2.65 (overlapping signals, 5H), 2.35-2.43 (br d, 1H), 2.26-2.35 (br d, 1H), 1.61-2.05 (overlapping signals, 24H), 1.11-1.60 (overlapping signals, 16H)

$^{13}$C NMR (CDCl$_3$) (1:1 mixture of cis-trans amide rotamers) δ (ppm) 205.4, 203.6, 169.4, 168.6, 168.1, 166.9, 153.1, 137.1, 137.0, 136.2, 136.1, 105.2, 105.2, 60.8, 56.7, 56.0, 56.0, 51.7, 46.9, 46.4, 44.2, 39.6, 39.1, 39.0, 33.4, 33.4, 31.3, 31.2, 29.7, 27.6, 27.1, 26.8, 26.6, 26.2, 25.8, 25.6, 25.6, 25.4, 25.2, 25.1, 24.9, 24.7, 20.6, 20.4

LC Mass Spectroscopy
Observed m/z 475.2 (M+H). Observed 498.0 (M+Na), 457.3, 250.1

Synthesis

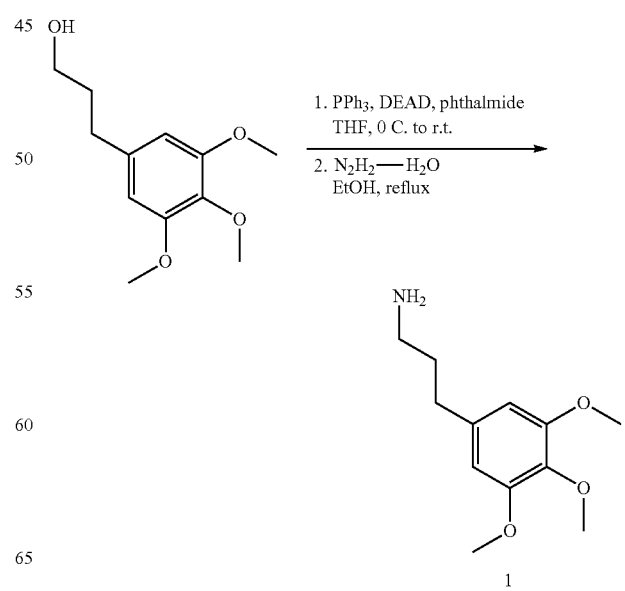

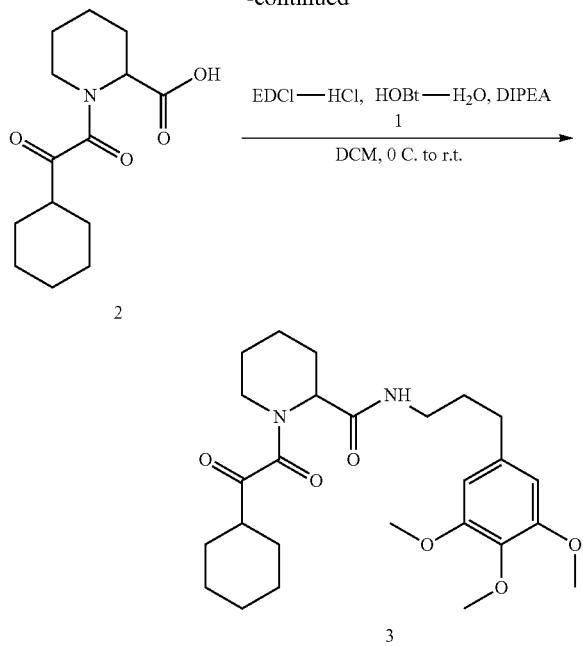

3-(3,4,5-trimethoxyphenyl)propan-1-amine (1) was produced from 3-(3,4,5-trimethoxy phenyl)propan-1-ol using diethyl azodicarboxylate (DEAD, 40% in toluene) following the Mitsunobu Reaction (hydrogen azide produced via triphenylphosphine and phthalimide in THF).

To a flame dried 100 mL round bottom flask was added triphenylphosphine (936 mg, 3.55 mmol) and phthalimide (484 mg, 3.23 mmol). A stirbar was added, and the flask was sealed using a rubber septa under nitrogen. Dry THF (10 mL) was added via syringe and the stirred mixture was cooled in an ice bath. Once cooled, a solution of 3-(3,4,5-trimethoxyphenyl)propan-1-ol (730 mg, 3.23 mmol) in dry THF (20 mL) was added via syringe, resulting in a clear, colorless solution. Diethyl azodicarboxylate (DEAD, 40% in toluene, 0.65 mL, 3.55 mmol) was added dropwise via syringe. The resulting yellow solution was allowed to warm to room temperature under nitrogen while stirring. The reaction was stirred at room temperature for 17 h. The solvent was evaporated under reduced pressure, and the crude yellow solid product (3.089 g) was used without purification.

To a 3-necked flask (500 mL) equipped with a condenser and internal thermocouple was charged the crude phthalimide in ethanol (180 mL). To the resulting slurry was added hydrazine monohydrate (2.25 mL, 26.1 mmol) at room temperature. The reaction was placed under a nitrogen sweep and heated to reflux (78° C.) for two hours. The reaction was cooled to room temperature and the solvent evaporated under reduced pressure. The resulting solvent-wetted yellow solid (8.8 g) was loaded onto SCX (strong cation exchange) resin (15 g) and eluted sequentially with DCM (60 mL), MeOH (70 mL), $H_2O$ (40 mL), MeOH (50 mL), to remove the impurities. The desired compound was then eluted using 1N $NH_3$ in MeOH (200 mL). After evaporating the solvent, the column purified material was dissolved in DCM (5 mL) and washed with $H_2O$ (3×5 mL). The organic layer was dried ($MgSO_4$), filtered and evaporated, resulting in the desired amine 1 (217.6 mg, 0.97 mmol, 30% yield for two steps).

3-(3,4,5-trimethoxyphenyl)propyl-1-(2-cyclohexyl-2-oxoacetyl)piperidine-2-amide) (3): To a 40 mL glass vial were added acid 2 (261 mg, 0.97 mmol), EDCl.HCl (205 mg, 1.06 mmol), and HOBt.$H_2O$ (165 mg, 1.06 mmol). The headspace purged with nitrogen and the vial capped with a septa. Dry DCM (5.0 mL) was added via syringe, resulting in a clear yellow solution. The vial was cooled in an ice-water bath with stirring. Once cooled, a solution of 1 (217.6 mg, 0.97 mmol) and DIPEA (0.65 mL, 3.88 mmol) in dry DCM (1.0 mL) was added. The reaction was stirred at 0° C. for 15 minutes after completing the addition, then warmed to room temperature. The reaction was stirred under nitrogen for 22 hours, after which TLC (7:3:1 v/v/v DCM:MeOH:$NH_4OH$) showed consumption of the reactants. The reaction was worked up by washing with water (2×6 mL). The aqueous part was back extracted with DCM (1×6 mL). The combined organic layers were combined, dried ($MgSO_4$), filtered and evaporated. The desired compound was isolated on a 45 g silica column, using a EtOAc-hexanes gradient, affording the desired amide 3 as a thick, opaque oil (365.5 mg, 80% yield).

Synthesis of B3

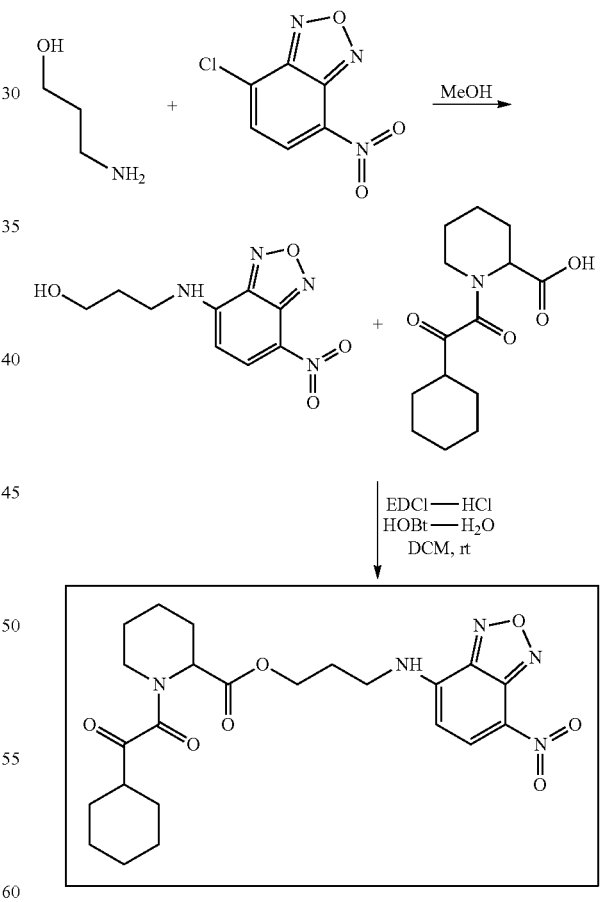

Chemical Name: 2-(7-nitrobenzo[c][1,2,5]oxadiazol-4-ylamino)ethyl 1-(2-cyclohexyl-2-oxoacetyl)piperidine-2-carboxylate Formula: $C_{22}H_{27}N_5O_7$

MW: 473.48

Appearance: Orange solid

Soluble in: DMSO, MeOD, CDCl$_3$
NMR Data
$^1$H NMR 400 MHz (CDCl$_3$) (3:1 mixture of amide rotamers) δ (ppm) 8.50 (d, 2H), 7.00 (br t 1H) 6.75 (br t, 1H), 6.25-6.26 (d, 1H, J=8.6 Hz), 6.23-6.26 (d, 1H, J=8.6 Hz), 5.20 (m, 1H), 4.55-4.62 (m, 1H), 4.48-4.52 (t, 4H, J=5.3 Hz), 4.43-4.48 (m, 1H), 3.78-3.95 (overlapping signals, 4H), 3.48-3.56 (br d, 2H), 3.11-3.22 (td, 2H, J=13.1 Hz, 3.3 Hz), 2.99-3.10 (m, 1H), 2.85-2.96 (m, 2H), 2.20-2.35 (m, 2H), 1.60-2.04 (overlapping signals, 19H), 1.15-1.58 (overlapping signals 22H)
$^{13}$C NMR (CDCl$_3$) (3:1 mixture of amide rotamers) δ (ppm) 170.4, 168.1, 136.1, 62.6, 56.3, 51.9, 47.0, 46.7, 44.2, 42.9, 39.6, 29.7, 27.4, 27.2, 26.9, 26.7, 26.5, 25.8, 25.7, 25.6, 25.3, 25.2, 24.9, 24.8, 24.1, 20.9, 20.5
LC Mass Spectroscopy
Observed m/z 474.1 (M+H).
Synthesis:

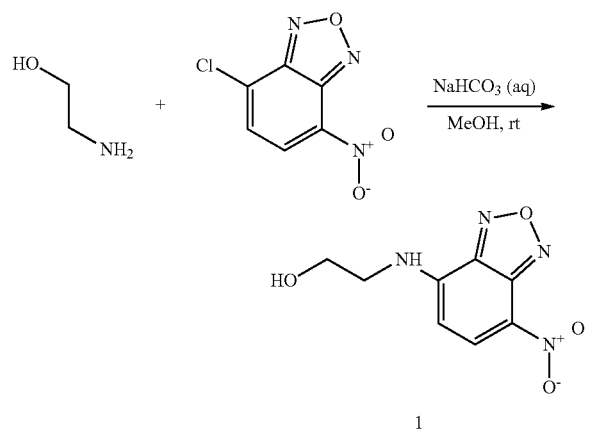

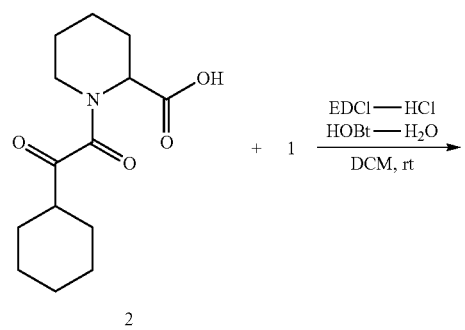

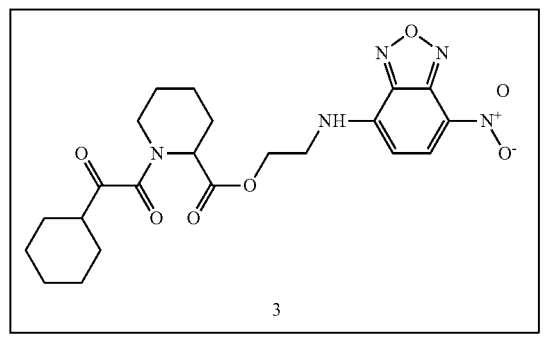

3-[(7-nitro-2,1,3-benzoxadiazol-4-yl)amino]ethanol (1): To a 100 mL round bottom flask was added 4-chloro-7-nitrobenz-2-oxa-1,3-diazole (1.0039 g, 5.01 mmol), 40 mL MeOH and aqueous NaHCO$_3$ (20 mL, 0.3 M). To the stirred red-yellow solution 2-aminopropanol was added (313.5 mg, 5.16 mmol). Upon addition, the reaction darkened to a brown color and a precipitate formed. After stirring at room temperature for 22 hours, TLC (1:1 EtOAc:hexanes, p-Anisaldehyde) indicated formation of a new product (Rf=0.61). The solvent was evaporated under reduced pressure and chased with toluene, then evaporated once more, resulting in a brown solid. The crude material was adsorbed onto 10 g silica gel with MeOH and chromatography (100% EtOAc) afforded the desired compound as a red solid (610 mg, 54% yield). The compound was observed to fluoresce a bright yellow-green in EtOAc.

3-(7-nitrobenzo[c][1,2,5]oxadiazol-4-ylamino)propyl1-(2-cyclohexyl-2-oxoacetyl)piperidine-2-carboxylate (3): To a 20 mL glass vial were added acid 2 (150.3 mg, 0.62 mmol), EDCI-HCl (122.2 mg, 0.64 mmol), and HOBt-H$_2$O (98.1 mg, 0.64 mmol). The headspace was purged with nitrogen and the vial capped with a septum. Dry DCM (3.5 mL) was added via syringe, resulting in a clear yellow solution. The vial was cooled in an ice-water bath with stirring. Once cooled, a heterogeneous mixture of 1 (150.3 mg, 0.56 mmol) and DIPEA (0.38 mL, 2.24 mmol) in dry DCM (1.5 mL) was added. The reaction was stirred at 0° C. for 15 minutes after completing the addition, then warmed to room temperature. The reaction was stirred under nitrogen for 18 hours, after which TLC (1:1 EtOAc:hexanes) showed product formation (R$_f$=0.29). The reaction was worked up by washing with water (2×5 mL). The combined organic layers were dried (MgSO$_4$), filtered and evaporated. The desired compound was isolated on a 25 g silica column, using EtOAc-hexanes (1:1), affording the desired ester 3 as an orange solid (129.8 mg, 49% yield). The compound was observed to fluoresce in EtOAc (yellow-green), DMSO (red) and MeOH (red).

Synthesis of B4

Figure 4:
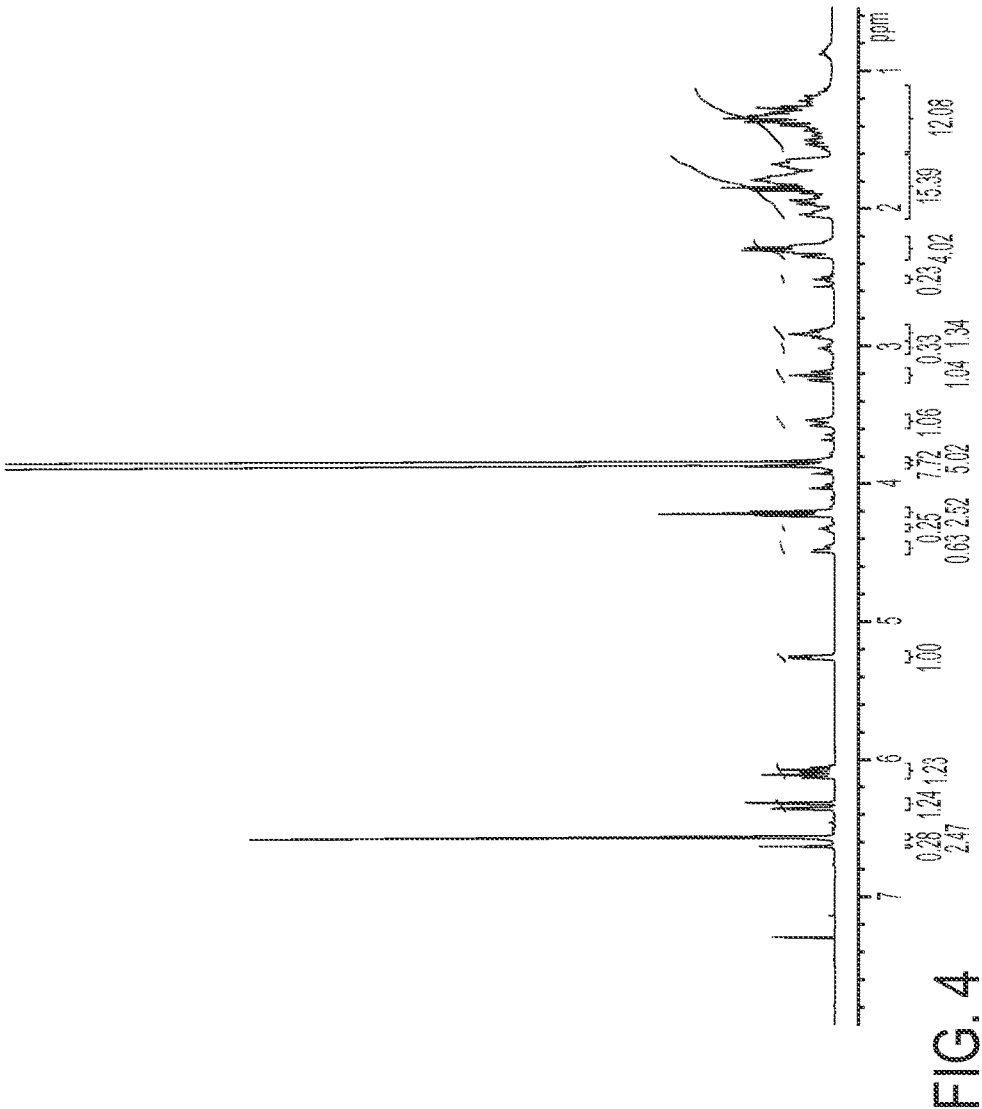
FIG. 4: $^1$H NMR spectra for compound B4.

NMR Data
$^1$H NMR is shown in FIG. 4.
$^{13}$C NMR (CDCl$_3$) δ (ppm) (4:1 mixture of cis trans amide rotamers) 203.6, 203.5, 170.5, 170.3, 167.8, 166.7, 152.9, 137.4, 133.2, 130.9, 128.4, 108.7, 103.0, 77.4, 77.1, 76.8, 65.0, 64.8, 64.2, 60.8, 56.3, 56.1, 56.0, 55.9, 51.6, 47.1, 46.7, 46.4, 43.8, 39.4, 39.1, 29.1, 28.2, 27.6, 27.5, 27.3, 27.0, 26.7, 26.4, 25.8, 25.7, 25.5, 25.3, 25.3, 25.2, 25.0, 24.4, 21.1, 20.9, 16.0.
LC Mass Spectroscopy
Observed m/z 502.2 (M+H)

Synthesis of B5

Figure 5:
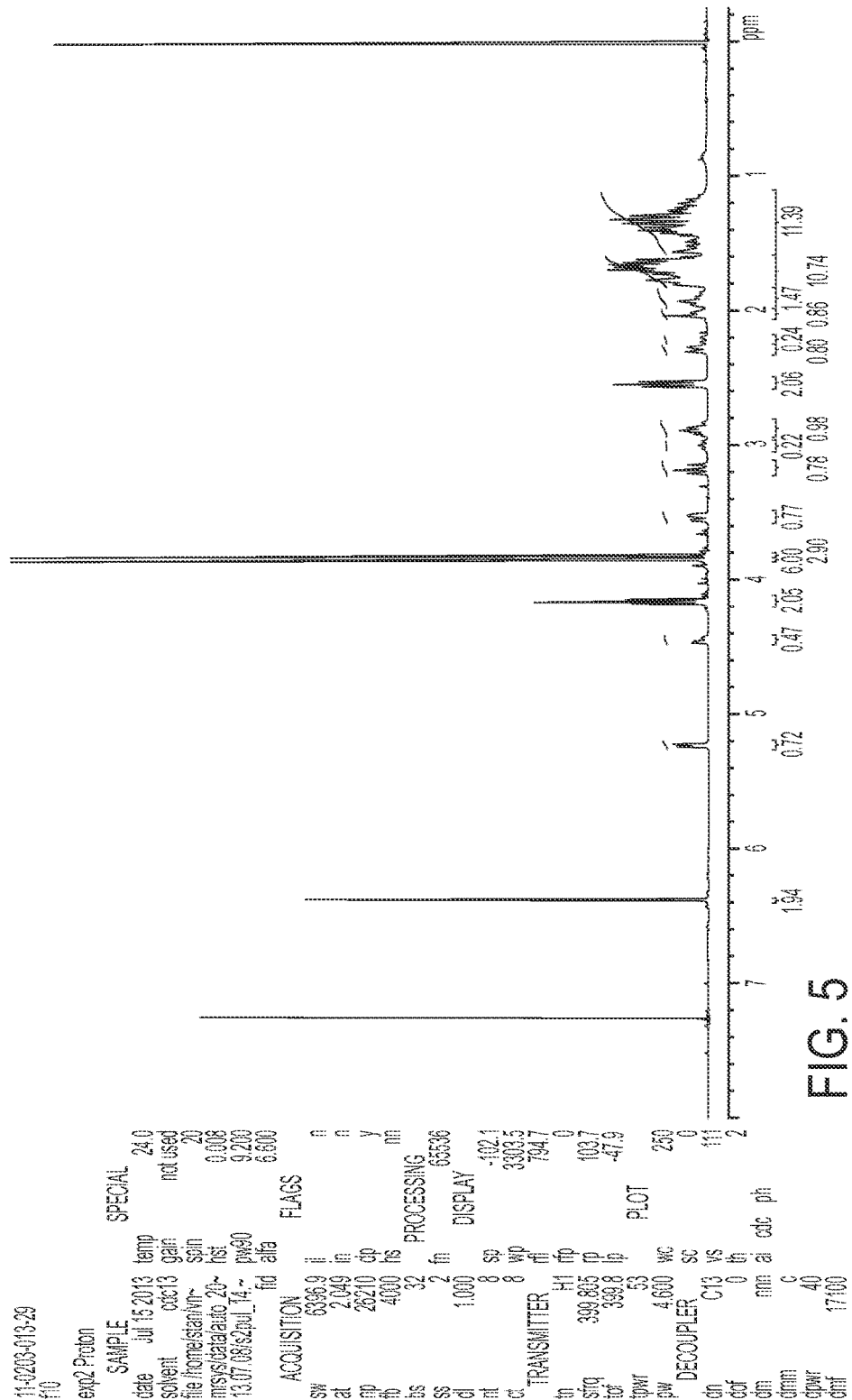
FIG. 5: $^1$H NMR spectra for compound B5.

NMR Data $^1$H NMR is shown in FIG. 5

$^{13}$C NMR (CDCl$_3$) δ (ppm) (4:1 mixture of cis trans amide rotamers) 203.6, 203.5, 170.5, 170.3, 167.8, 166.7, 153.0, 138.0, 136.0, 105.2, 77.4, 77.1, 76.8, 65.5, 65.4, 60.8, 56.3, 56.0, 55.9, 51.6, 47.1, 46.7, 46.4, 43.8, 39.3, 36.2, 31.0, 28.4, 27.4, 27.3, 27.0, 26.7, 26.4, 25.8, 25.7, 25.5, 25.3, 25.3, 25.2, 25.0, 24.4, 21.1, 20.9.

LC Mass Spectroscopy

Observed m/z 504.2 (M+H).

All of the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Babbitt, et al., Cell, 121, 553-65, 2005.
Busse, et al., Cancer, 112:659-670, 2008.
Chen and Madura, Cancer Res., 65:5599-5606, 2005.
Crawford, et al., J. Cell Commun. Signal., 5:101-110, 2011.
de Bettignies and Coux, Biochimie, 92:1530, 2010.
Engel, et al., Cancer Investigation, 25:733-737, 2007.
Gaczynska, et al., Biochemistry, 42:8663-70, 2003.
Gaczynska and Osmulski, Methods in Cell Biology, 90:39-60, 2009.
Goodey and Benkovic, Nature Chemical Biology, 4:474-482, 2008.
Groll, et al., Chembiochem, 6:222, 2005.
Gunasekaran, et al., Proteins, 57:433, 2004.
Handbook of Pharmaceutical Salts: Properties, and Use, Stahl and Wermuth Eds.), Verlag Helvetica Chimica Acta, 2002.
Jankowska, et al., Biopolymers, 93:481, 2010.
Jankowska, et al., Current Pharmaceutical Design, in press, 2013.
Kisselev, et al., J. Biol. Chem., 278:35869-77, 2003.
Klejinen, et al., Nature Structural & Molecular Biology, 14:1180-1188, 2007.

Kraus, et al., *Leukemia*, 21:84-9, 2007.
Lander, et al., *Nature*, 482:186-191, 2012.
Liang, et al., *Acta Crystallographica Section D: Biological Crystallography*, 55:736, 1999.
Liu, et al., *Molecular Cell*, 24:39-50, 2006.
Ma and Blenis, *Nature Reviews in Molecular and Cell Biology*, 10:307-318, 2009.
Madura, K. *Nature*, 259:787-788, 2009.
*March's Advanced Organic Chemistry: Reactions, Mechanisms, and Structure*, 2007.
Orlowski and Kuhn, *Clinical Cancer Research*, 14:1649-1657, 2008.
Osmulski et al., *Structure*, 17:1137, 2009.
Rodriguez, et al., *Mech. Ageing Dev.*, 131:144-155, 2010.
Rosenzweig, et al., *Nature Struct. Mol. Biol.*, 15:573-580, 2008.
Smith, et al., *Molecular Cell*, 27:731-744, 2007.
Whitehurst et al., *Nature*, 446:815-819, 2007.
Yamaguchi, et al, *Cancer Science*, 100:1668-1674, 2009.
Yang et al., *Ann Oncol*, 17(5):813-817, 2006.

The invention claimed is:

1. A compound of the formula:

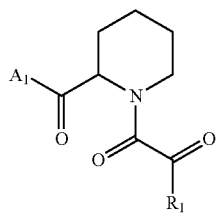
(I)

wherein:
$A_1$ is

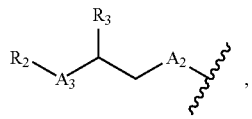

wherein:
$A_2$ is —O—;
$A_3$ is alkanediyl$_{(C \leq 6)}$, alkenediyl$_{(C \leq 6)}$, or a substituted version of either of these groups;
$R_2$ is

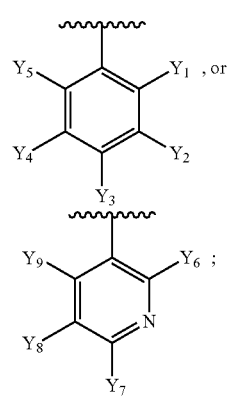

wherein:
$Y_1$, $Y_5$, $Y_6$, $Y_7$, $Y_8$, and $Y_9$ are each independently hydrogen, hydroxy, phosphate, halo, alkyl$_{(C \leq 12)}$, alkoxy$_{(C \leq 12)}$, acyloxy$_{(C \leq 12)}$, heteroaryl$_{(C \leq 12)}$, acyl$_{(C \leq 12)}$, alkylamino$_{(C \leq 12)}$, dialkylamino$_{(C \leq 12)}$, or a substituted version of any of these groups, and $Y_2$ and $Y_4$ are alkoxy$_{(C \leq 12)}$ or substituted alkoxy$_{(C \leq 12)}$, and $Y_3$ is alkoxy$_{(C < 12)}$;
$R_3$ is hydrogen, alkyl$_{(C \leq 8)}$, or a substituted alkyl$_{(C \leq 8)}$; and
$R_1$ is

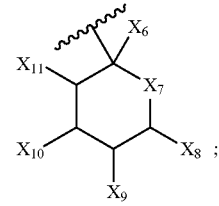

wherein:
$X_6$ is hydrogen or hydroxy;
$X_7$ is O, NH, or C(R$_5$)$_2$;
$X_8$ is hydrogen, hydroxy, phosphate, halo, alkyl$_{(C \leq 6)}$, alkoxy$_{(C \leq 6)}$, acyloxy$_{(C \leq 6)}$, heteroaryl$_{(C \leq 12)}$, acyl$_{(C \leq 6)}$, alkylamino$_{(C \leq 6)}$, dialkylamino$_{(C \leq 6)}$, or a substituted version of any of these groups;
$X_9$, $X_{10}$, $X_{11}$, and $R_5$ are each independently hydrogen, hydroxy, phosphate, halo, alkyl$_{(C \leq 12)}$, alkoxy$_{(C \leq 12)}$, acyloxy$_{(C \leq 12)}$, heteroaryl$_{(C \leq 12)}$, acyl$_{(C \leq 12)}$, alkylamino$_{(C \leq 12)}$, dialkylamino$_{(C \leq 12)}$, or a substituted version of any of these groups.

2. The compound of claim 1, wherein the formula is further defined as:

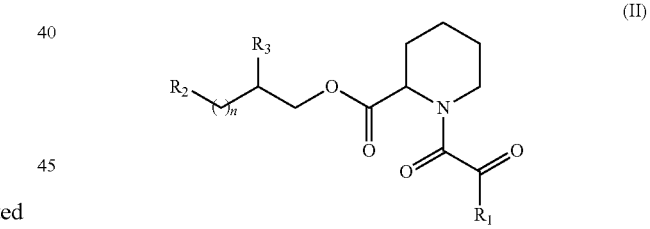
(II)

wherein:
$R_1$ is as defined above;
n is 1-4;
$R_2$ is

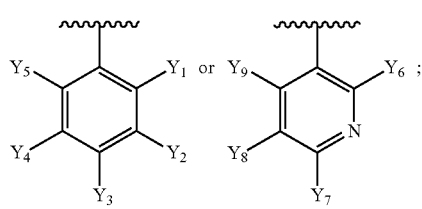

wherein:
$Y_1$, $Y_5$, $Y_6$, $Y_7$, $Y_8$, and $Y_9$ are each independently hydrogen, hydroxy, phosphate, halo, alkyl$_{(C \leq 12)}$, alkoxy$_{(C \leq 12)}$, acyloxy$_{(C \leq 12)}$, heteroaryl$_{(C \leq 12)}$, acyl$_{(C≤12)}$, alkylamino$_{(C≤12)}$, dialkylamino$_{(C≤12)}$, or a substituted version of any of these groups, and $Y_2$ and $Y_4$ are alkoxy$_{(C≤12)}$ or substituted alkoxy$_{(C≤12)}$, and $Y_3$ alkoxy$_{(C<12)}$;

$R_3$ is hydrogen, alkyl$_{(C≤8)}$, or a substituted alkyl$_{(C≤8)}$;

or a pharmaceutically acceptable salt, thereof.

3. The compound according to claim 1, wherein $X_7$ is $C(R_5)_2$.

4. The compound of claim 3, wherein $R_5$ is hydrogen.

5. The compound according to claim 1, wherein $X_8$, $X_9$, and $X_{10}$ are hydrogen.

6. The compound according to claim 1, wherein $X_{11}$ is hydrogen.

7. The compound according to claim 1, wherein $R_2$ is

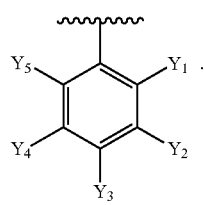

8. The compound of claim 7, wherein $Y_1$ is hydrogen.

9. The compound according to claim 1, wherein $R_2$ is

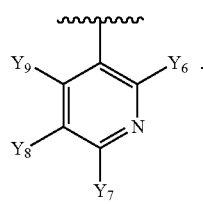

10. The compound according to claim 1, wherein $R_3$ is hydrogen.

11. The compound according to claim 1, wherein $R_3$ is alkyl$_{(C≤8)}$.

12. The compound of claim 11, wherein $R_3$ is methyl.

13. The compound according to claim 1, further defined as:

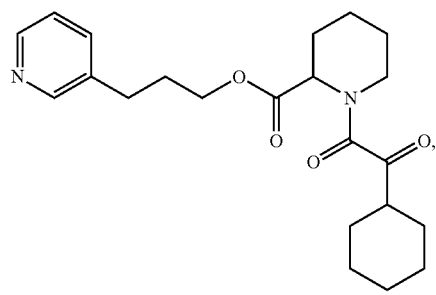

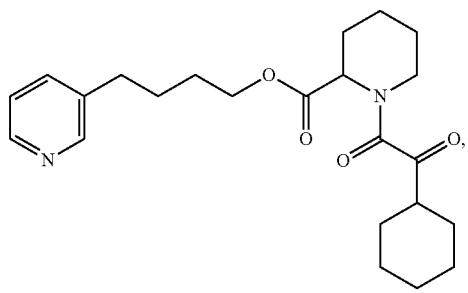

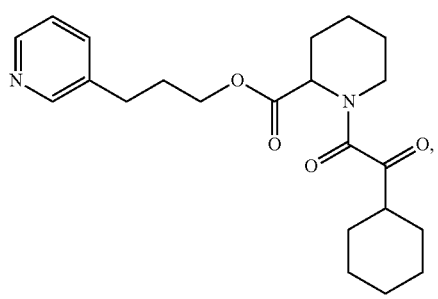

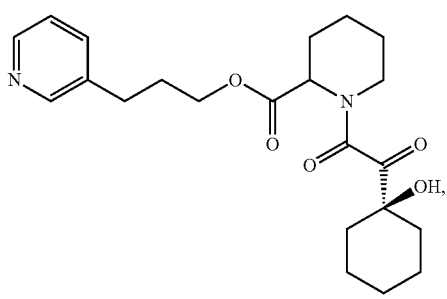

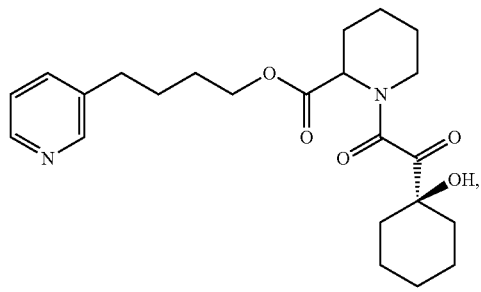

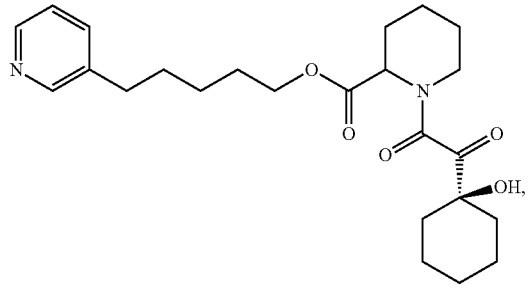

57
-continued
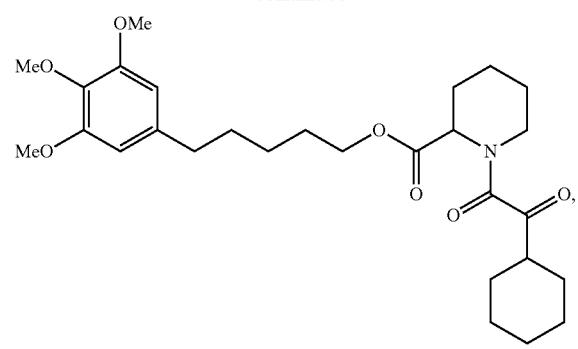
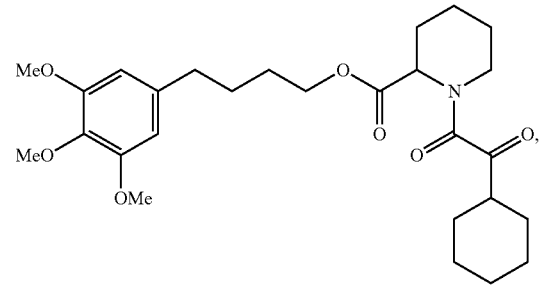
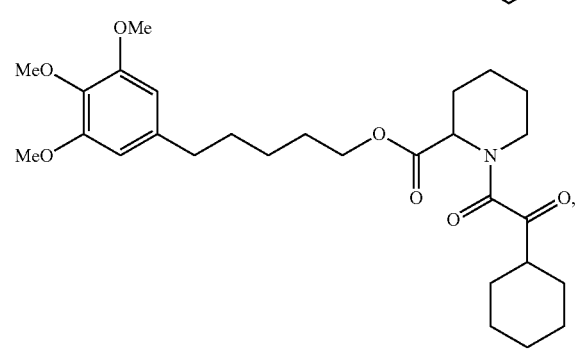
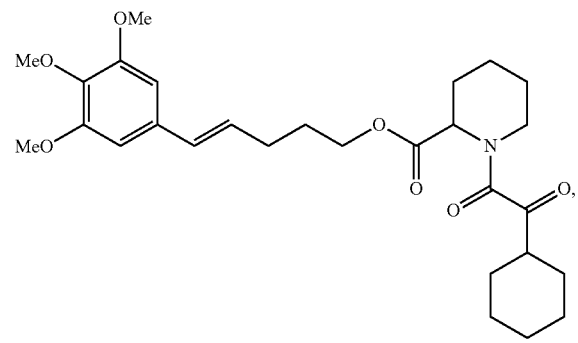
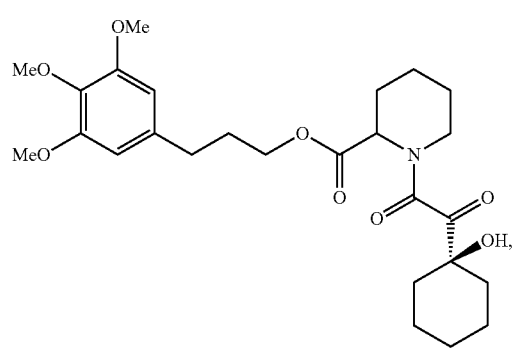
58
-continued
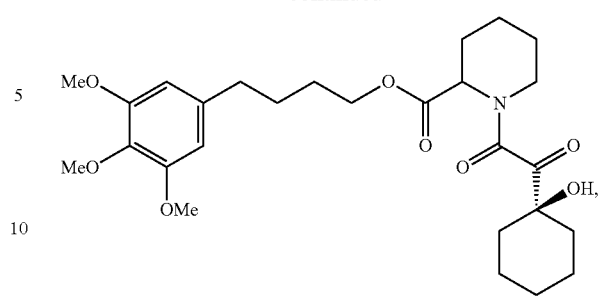
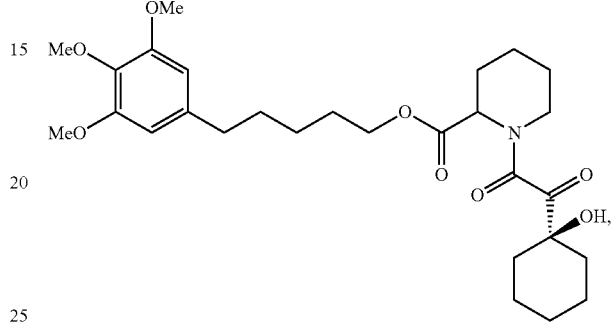
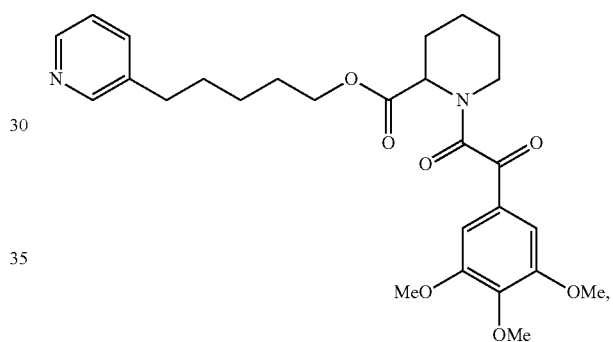
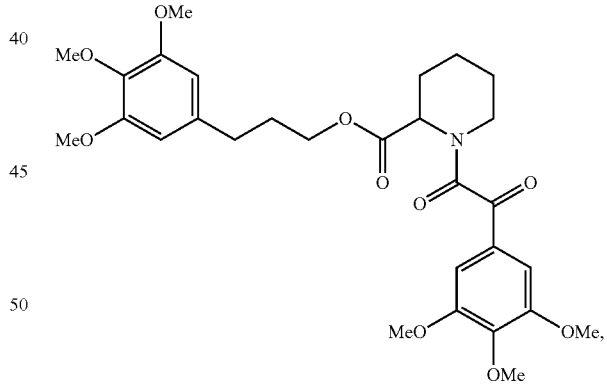
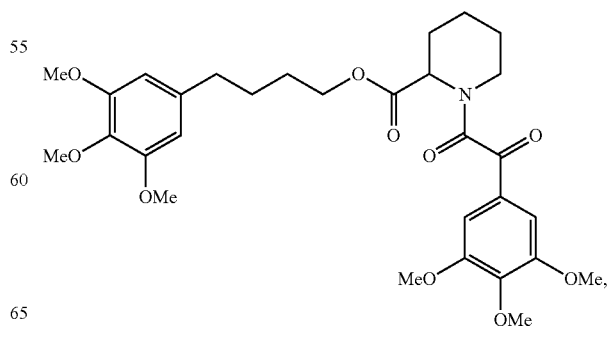

-continued
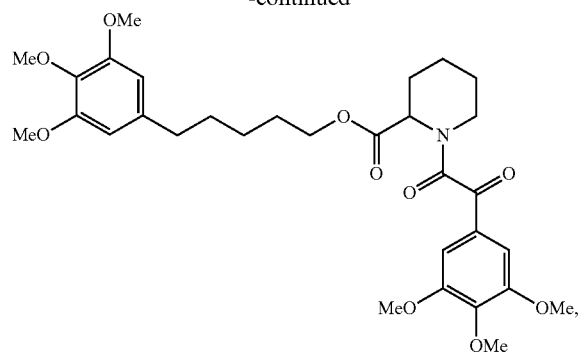
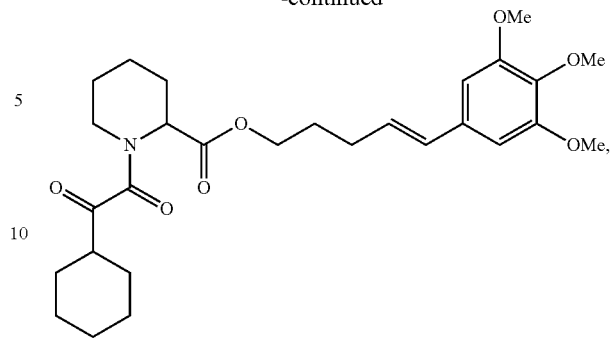
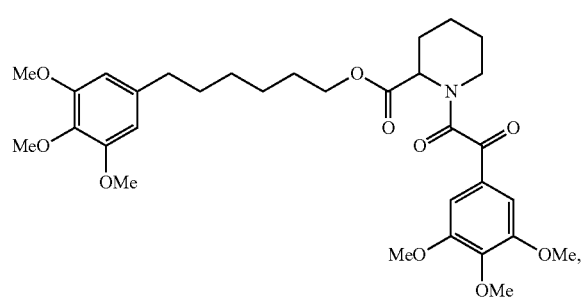
or
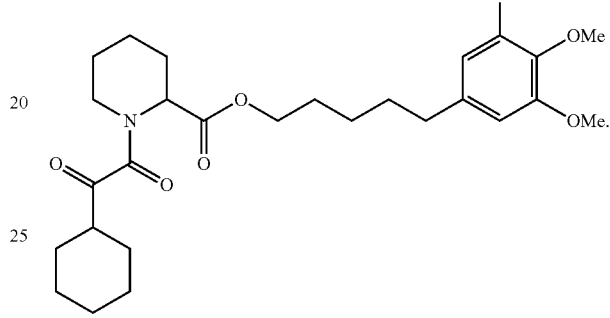
or a pharmaceutically acceptable salt thereof.
14. The compound of claim 13, wherein the formula is further defined as:
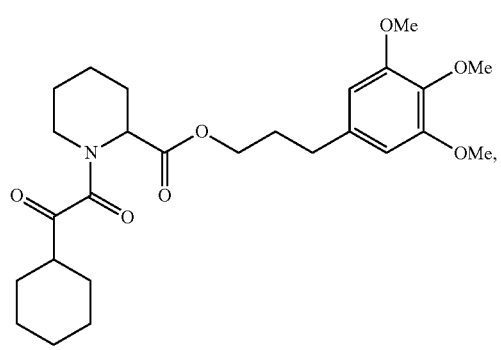
15. The compound of claim 14, wherein the formula is further defined as:
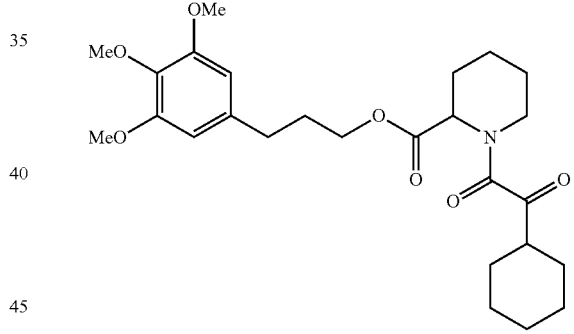
or a pharmaceutically acceptable salt thereof.
16. A pharmaceutical composition comprising a compound of claim 1 and an excipient.
* * * * *

UNITED STATES PATENT AND TRADEMARK OFFICE
CERTIFICATE OF CORRECTION

PATENT NO. : 10,167,259 B2
APPLICATION NO. : 14/896984
DATED : January 1, 2019
INVENTOR(S) : Pawel A. Osmulski et al.

Page 1 of 1

It is certified that error appears in the above-identified patent and that said Letters Patent is hereby corrected as shown below:

In the Claims

In Claim 13, Column 56, Lines 15-29, delete the entire contents and insert:

-- 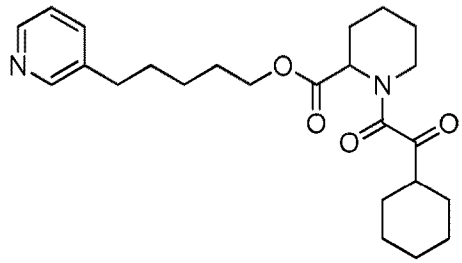 -- therefor.

In Claim 13, Column 57, Lines 1-14, delete the entire contents and insert:

-- 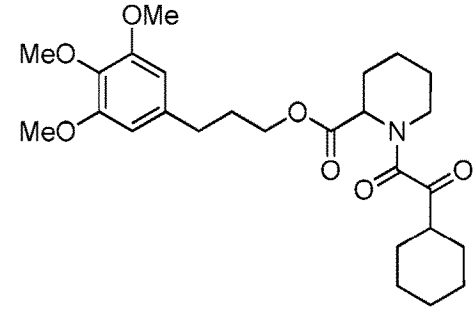 -- therefor.

Signed and Sealed this
Nineteenth Day of February, 2019

Andrei Iancu
*Director of the United States Patent and Trademark Office*